(12) United States Patent
Ram et al.

(10) Patent No.: US 9,475,864 B2
(45) Date of Patent: Oct. 25, 2016

(54) **METHODS, COMPOSITIONS AND VACCINES RELATING TO *NEISSERIA MENINGITIDIS* ANTIBODIES**

(75) Inventors: Sanjay Ram, Worcester, MA (US); Tathagat Duttaray, Worcester, MA (US); Peter A. Rice, Southborough, MA (US); Lisa A. Lewis, Hudson, MA (US); Sunita Gulati, Spencer, MA (US)

(73) Assignee: University of Massachusetts, Boston, MA (US)

( * ) Notice: Subject to any disclaimer, the term of this patent is extended or adjusted under 35 U.S.C. 154(b) by 255 days.

(21) Appl. No.: 13/062,181

(22) PCT Filed: Sep. 4, 2009

(86) PCT No.: PCT/US2009/005019
§ 371 (c)(1),
(2), (4) Date: May 16, 2011

(87) PCT Pub. No.: WO2010/027499
PCT Pub. Date: Mar. 11, 2010

(65) Prior Publication Data
US 2011/0229522 A1    Sep. 22, 2011

Related U.S. Application Data

(60) Provisional application No. 61/094,578, filed on Sep. 5, 2008.

(51) Int. Cl.
*A61K 39/095*    (2006.01)
*A61K 39/00*     (2006.01)
*C07K 16/12*     (2006.01)
*C07K 14/22*     (2006.01)
*G01N 33/569*    (2006.01)

(52) U.S. Cl.
CPC ......... *C07K 16/1217* (2013.01); *A61K 39/095* (2013.01); *C07K 14/22* (2013.01); *G01N 33/569* (2013.01); *A61K 2039/505* (2013.01); *A61K 2039/522* (2013.01); *G01N 2333/22* (2013.01)

(58) Field of Classification Search
None
See application file for complete search history.

(56) References Cited

U.S. PATENT DOCUMENTS

| | | | |
|---|---|---|---|
| 4,271,147 A | 6/1981 | Helting et al. | 424/250.1 |
| 4,601,903 A | 7/1986 | Frasch | 424/250.1 |
| 6,627,204 B1 | 9/2003 | Ruelle | 424/250.1 |
| 6,914,131 B1 | 7/2005 | Scarlato et al. | 536/23.1 |
| 7,018,636 B1 | 3/2006 | Bhattacharjee et al. | 424/197.11 |
| 7,025,963 B1 | 4/2006 | Bhattacharjee et al. | 424/150.1 |
| 7,118,757 B1 | 10/2006 | Seid, Jr. et al. | 424/250.1 |
| 2004/0249125 A1 | 12/2004 | Pizza et al. | 530/350 |
| 2006/0251669 A1 | 11/2006 | Chakrabarty et al. | 435/6 |

FOREIGN PATENT DOCUMENTS

EP    0449958 B2    11/2002
EP    1534342       6/2005

OTHER PUBLICATIONS

Wu et al. Infect. Immun. 73: 8444-8448, 2005.*
Hong et al. Cell Cycle 5:15, 1633-1641, Aug. 2006.*
Claus et al. J. Bacteriol. 182: 1296-1303, 2000.*
Trees et al. J. Infect. Dis. 161: 336-339, 1990.*
Apicella, M. A. et al (1986) "Bactericidal Antibody Response of Normal Human Serum to the Lipooligosaccharide of Neisseria gonorrhoeae," *The Journal of Infectious Diseases* 153(3), 520-526.
Baehr, W. et al. (1989) "The virulence-associated gonococcal H.8 gene encodes 14 tandemly repeated pentapeptides," *Molecular Microbiology* 3(1), 49-55.
Bjune, G. et al. (1991) "Effect of outer membrane vesicle vaccine against group B meningococcal disease in Norway," *Lancet* 338(8775), 1093-1096.
Borrow, R. et al. (2005) "Meningococcal surrogates of protection—serum bactericidal antibody activity," *Vaccine* 23(17-18), 2222-2227.
Cannon, J. G. (1989) "Conserved lipoproteins of pathogenic *Neisseria* species bearing the H.8 epitope: lipid-modified azurin and H.8 outer membrane protein," *Clinical Microbiology Reviews* 2(Suppl), S1-S4.
Cannon, J. G. et al. (1984) "Monoclonal antibody that recognizes an outer membrane antigen common to the pathogenic *Neisseria* species but not to most nonpathogenic *Neisseria* species," *Infection and Immunity* 43(3), 994-999.
Dutta Ray, T. et al. (2011) "Novel Blocking Human IgG Directed against the Pentapeptide Repeat Motifs of *Neisseria meningitidis* Lip/H.8 and Laz Lipoproteins," *Journal of Immunology* 186(8), 4881-4894.
Findlow, H. et al (2007) "Pulmonary Complications of Interpandemic Influenza A in Hospitalized Adults," *Journal of Infectious Diseases* 195(7), 1071-1077.
Finne, J. et al. (1983) "Antigenic Similarities between Brain Components and Bacteria Causing Meningitis," *Lancet* 322(8346), 355-357.
Fisette, P. L. et al. (2003) "The Lip Lipoprotein from Neisseria gonorrhoeae Stimulates Cytokine Release and NF-κB Activation in Epithelial Cells in a Toll-like Receptor 2-dependent Manner," *Journal of Biological Chemistry* 278(47), 46252-46260.
Fletcher, L. D. et al. (2004) "Vaccine Potential of the *Neisseria meningitidis* 2086 Lipoprotein," *Infection and Immunity* 72(4), 2088-2100.
Frasch, C. E. et al. (2009) "Bactericidal antibody is the immunologic surrogate of protection against meningococcal disease," *Vaccine* 27, Supplement 2(0), B112-B116.
Genbank. "Accession # NP_274540."

(Continued)

*Primary Examiner* — S. Devi
(74) *Attorney, Agent, or Firm* — Medlen & Carroll, LLP

(57) ABSTRACT

The invention provides compositions and methods for screening subjects at risk for contracting meningococcal disease and/or at risk for failing to elicit an immunogenic response to a vaccine against *Neisseria meningitidis*. The invention also provides kits for carrying out these screens, and improved vaccines against *Neisseria meningitidis*.

8 Claims, 16 Drawing Sheets

(56) References Cited

OTHER PUBLICATIONS

Genbank. "Accession # NP_274531."
Giuliani, M. M. et al. (2006) "A universal vaccine for serogroup B meningococcus," *Proceedings of the National Academy of Sciences* 103(29), 10834-10839.
Goldschneider, I. et al. (1969) "Human Immunity to the Meningococcus: I. The Role of Humoral Antibodies," *Journal of Experimental Medicine* 129(6), 1307-1326.
Gotschlich, E. C. et al. (1987) "Identification and gene structure of an azurin-like protein with a lipoprotein signal peptide in Neisseria gonorrhoeae," *FEMS Microbiology Letters* 43(3), 253-255.
Griffiss, J. M. et al. (1977) "Immunoepidemiology of Meningococcal Disease in Military Recruits. II. Blocking of Serum Bactericidal Activity by Circulating IgA Early in the Course of Invasive Disease," *Journal of Infectious Diseases* 136(6), 733-739.
Hoang, L. M. N. et al. (2005) "Rapid and Fatal Meningococcal Disease Due to a Strain of *Neisseria meningitidis* Containing the Capsule Null Locus," *Clinical Infectious Diseases* 40(5), e38-e42.
Jarvis, G. A. et al. (1991) "Human IgA1 blockade of IgG-initiated lysis of *Neisseria meningitidis* is a function of antigen-binding fragment binding to the polysaccharide capsule," *Journal of Immunology* 147(6), 1962-1967.
Joiner, K. A. et al. (1985) "Mechanism of action of blocking immunoglobulin G for Neisseria gonorrhoeae," *The Journal of Clinical Investigation* 76(5), 1765-1772.
Kawula, T. H. et al. (1987) "Localization of a conserved epitope and an azurin-like domain in the H.8 protein of pathogenic Neisseria," *Molecular Microbiology* 1(2), 179-185.
McLeod Griffiss, J. et al. (1975) "Bactericidal Activity of Meningococcal Antisera: Blocking by IgA of Lytic Antibody in Human Convalescent Sera," *Journal of Immunology* 114(6), 1779-1784.
McNicholas, A. et al. (2008) "Surveillance of vaccine breakthrough cases following MeNZB vaccination," *The New Zeland Medical Journal* 121(1272), 38-49.
Munkley, A. et al. (1991) "Blocking of bactericidal killing of *Neisseria meningitidis* by antibodies directed against class 4 outer membrane protein," *Microbial Pathogenesis* 11(6), 447-452.
Plummer, F. A. et al. (1993) "Antibody to Rmp (outer membrane protein 3) increases susceptibility to gonococcal infection," *The Journal of Clinical Investigation* 91(1), 339-343.
Rice, P. A. et al. (1986) "Immunoglobulin G antibodies directed against protein III block killing of serum-resistant Neisseria gonorrhoeae by immune serum," *Journal of Experimental Medicine* 164(5), 1735-1748.
Rosenqvist, E. et al. (1999) "Functional Activities and Epitope Specificity of Human and Murine Antibodies against the Class 4 Outer Membrane Protein (Rmp) of *Neisseria meningitidis*," *Infection and Immunity* 67(3), 1267-1276.
Strittmatter, W. et al. (1986) "Isolation and preliminary biochemical characterization of the gonococcal H.8 antigen," *Journal of Experimental Medicine* 164(6), 2038-2048.
Tettelin, H. et al. (2000) "Complete Genome Sequence of *Neisseria meningitidis* Serogroup B Strain MC58," *Science* 287(5459), 1809-1815.
Thomas, L. et al. (1943) "Investigations of Meningococcal Infection. III. The Bactericidal Action of Normal and Immune Sera for the Meningococcus 1," *The Journal of Clinical Investigation* 22(3), 375-385.
Thomas, L. et al. (1943) "Investigations of Meningococcal Infection II. Immunological Aspects 1," *The Journal of Clinical Investigation* 22(3), 361-373.
Trees, D. L. et al. (2000) "Use of the Neisserial Lipoprotein (Lip) for Subtyping Neisseria gonorrhoeae," *Journal of Clinical Microbiology* 38(8), 2914-2916.
Wedege, E. et al. (2007) "Functional and Specific Antibody Responses in Adult Volunteers in New Zealand Who Were Given One of Two Different Meningococcal Serogroup B Outer Membrane Vesicle Vaccines," *Clinical and Vaccine Immunology* 14(7), 830-838.
Welsch, J. A. et al. (2008) "Complement-Dependent Synergistic Bactericidal Activity of Antibodies against Factor H-Binding Protein, a Sparsely Distributed Meningococcal Vaccine Antigen," *Journal of Infectious Diseases* 197(7), 1053-1061.
Woods, J. P. et al, (1989) "Characterization of the neisserial lipid-modified azurin bearing the H.8 epitope," *Molecular Microbiology* 3(5), 583-591.
Woods, J. P. et al. (1989) "Conserved lipoprotein H.8 of pathogenic Neisseria consists entirely of pentapeptide repeats," *Molecular Microbiology* 3(1), 43-48.
Requirements for meningococcal polysaccharide vaccine. World Health Organization technical report series, No. 594 dated.
Wu, H.-J. et al. (2005) "Azurin of Pathogenic *Neisseria* spp. Is Involved in Defense against Hydrogen Peroxide and Survival within Cervical Epithelial Cells," *Infection and Immunity* 73(12), 8444-8448.
PCT International Search Report of International Application No. PCT/US2009/005019 dated Jul. 19, 2010.

* cited by examiner

Figure 11

LAZ MC58 NMB1533.

<u>MKAYLALISAAVIGLAA</u>CSQEPAAPAAEATPAAEAPASEAPAAEAAPAD
AAEAPAAGNCAATVESNDNMQFNTKDIQVSKACKEFTITLKHTGTQPKA
SMGHNLVIAKAEDMDGVFKDGVGAADTDYVKPDDARVVAHTKLIGGGEE
ASLTLDPAKLADGEYKFACTFPGHGALMNGKVTLVD

Figure 12

```
Lip_MC58    1    M K S L F A A A L L S L V L A A C G G E K A A E A P A A E      30
Laz_MC58    1    M K A Y L A L I S A A V I G L A A C S Q E P A A P A - A E A    29

Lip_MC58   31    A P A A E A P A T E A P A A E A A E A P A A E A P A A A E      60
Laz_MC58   30    T P A A E A P A S E A P A A E A P A D A E A P A A G N C        59

Lip_MC58   61    A A A T E A P A A E A A A A T E A P A A E A A A A T E A P A A E   90
Laz_MC58   60    A A T V E - - - - - - - - - - - - - - - - - - - - - - - - - -    64

Lip_MC58   91    A P A A E A A K                                                98
Laz_MC58   65    - - - - S N D N M Q F N T K D I Q V S K A C K E F T            86

Laz_MC58   87    I T L K H T G T Q P K A S M G H N L V I A K A E D M D G V F    116

Laz_MC58  117    K D G V G A A D T D Y V K P D D A R V V A H T K L I G G G E    146

Laz_MC58  147    E A S L T L D P A K L A D G E Y K F A C T F P G H G A L M N    176

Laz_MC58  177    G K V T L V D                                                  183
```

Figure 13

METHODS, COMPOSITIONS AND VACCINES RELATING TO *NEISSERIA MENINGITIDIS* ANTIBODIES

This application is the U.S. National stage filing of co-pending PCT Application No. PCT/US2009/005019, filed on Sep. 4, 2009, which claims priority to U.S. provisional Application Ser. No. 61/094,578, filed Sep. 5, 2008, now abandoned, which is herein incorporated by reference in its entirety for all purposes.

STATEMENT OF GOVERNMENT SUPPORT

This invention was made with government support under Grant Numbers AI 054544 and AI 32725 awarded by the National Institutes of Health (NIH). The government has certain rights in the invention.

FIELD OF THE INVENTION

The invention relates to compositions and methods for screening subjects at risk for contracting meningococcal disease and/or at risk for failing to elicit an immunogenic response to a vaccine against *Neisseria meningitidis*. The invention also relates to kits for carrying out these screening assays, and to improved vaccines against *Neisseria meningitidis*.

BACKGROUND OF THE INVENTION

*Neisseria meningitidis* is a leading cause of meningococcal disease, including meningitis and bacterial septicemia induced shock that affect children and young adults. Vaccines for protecting against meningococcal disease have been described; these include polysaccharide based vaccines, protein vaccines, and meningococcal outer membrane vesicle (OMV) vaccines. Protection against meningococcal disease is measured by the ability of antibody (Ab) in serum to mediate complement-dependent killing of the bacteria. A serum bactericidal titer of 1:4 or greater using human complement is considered protective against invasive disease (Goldschneider et al. (1969) J. Exp. Med. 129:1307-26). However, there is wide variation among individuals within a population in their ability to kill meningococci in complement-dependent bactericidal assays. In some instances, despite high levels of antibody binding, killing does not occur. Antibody directed against certain bacterial targets may not activate complement, and in some instances, may even block killing by otherwise bactericidal Ab.

Moreover, while capsular polysaccharide based vaccines have been successful in immunization against serogroups A, C, W and Y, currently there are no effective licensed vaccines available in the U.S. against serogroup B *Neisseria meningitidis*. Serogroup B capsular polysaccharide mimics a host molecule (neural-cell adhesion molecule, or N-CAM) (Finne et al., 1983. Lancet 2:355-357) and therefore is not immunogenic. Furthermore, there is concern that Abs elicited against serogroup B capsule may result in autoimmune damage to host neurons.

Efforts to combat epidemics caused by serogroup B meningococci have resulted in development of outer membrane vesicle vaccines. Once such epidemic occurred in Norway. The use of an outer membrane vesicle vaccine to counter this epidemic resulted in ~57% protection; this was not deemed sufficient to justify a public vaccination campaign (Bjune et al. 1991. Lancet 338:1093-1096). More recently, an outbreak of serogroup B meningococcal disease in New Zealand prompted the manufacture and use of outer membrane vesicle (OMV) vaccines prepared from *Neisseria meningitidis*, including the MenZB and MenBvac vaccines, that were 'tailor made' and used to combat a meningitis epidemic in New Zealand caused by serogroup B *Neisseria meningitidis* (Wedege E et al. Clin Vaccine Immunol. 2007; 14(7):830-8). However, breakthrough has occurred in cases who have been vaccinated; vaccine efficacy has been reported to be 75% (McNicholas et al., 2008, N Z Med J 121:38-46). Vaccine failures were not attributed to identifiable immunodeficiencies in the host.

Thus, there remains a need for methods for screening individuals at risk for contracting meningococcal disease and/or at risk for failing to elicit a bactericidal response to a vaccine against *Neisseria meningitidis*, as well as a need for improved immunogenic vaccines against meningococcal disease.

SUMMARY OF THE INVENTION

The invention provides compositions and methods for screening subjects at risk for contracting meningococcal disease and/or at risk for failing to elicit an immunogenic response to a vaccine against *Neisseria meningitidis*. The invention also provides kits for carrying out these screening assays, and improved vaccines against *Neisseria meningitidis*.

In one embodiment, the invention provides methods for identifying a mammalian subject at risk for infection by *Neisseria meningitidis*, comprising a) providing a biological sample from a subject, and b) detecting in the biological sample an antibody that specifically binds to a *Neisseria meningitidis* polypeptide selected from one or more of i) H.8, ii) antigenic portion of H.8, iii) Laz, and iv) antigenic portion of Laz. Without intending to limit the type of antigenic portion, in one embodiment, at least one of the antigenic portion of H.8 and the antigenic portion of Laz contains one or more amino acid that is conserved in *Neisseria meningitidis* H.8 and *Neisseria meningitidis* Laz. In another embodiment, at least one of the antigenic portion of H.8 and the antigenic portion of Laz contains amino acid sequence AAEAP. In a further embodiment, the level of the antibody that specifically binds to H.8 in the subject is higher than the level of the antibody in a subject that has not been infected with *Neisseria meningitidis* and has not been vaccinated against *Neisseria meningitidis*. In yet another embodiment, the level of the antibody that specifically binds to Laz in the subject is higher than the level of the antibody in a subject that has not been infected with *Neisseria meningitidis* and has not been vaccinated against *Neisseria meningitidis*.

Also without limiting the quantity of antibody detected by the invention's methods, in one embodiment, the level of the antibody that specifically binds to the antigenic portion of H.8 in the subject is higher than the level of the antibody in a subject that has not been infected with *Neisseria meningitidis* and has not been vaccinated against *Neisseria meningitidis*. In another embodiment, the level of the antibody that specifically binds to the antigenic portion of Laz in the subject is higher than the level of the antibody in a subject that has not been infected with *Neisseria meningitidis* and has not been vaccinated against *Neisseria meningitidis*.

The invention's methods are not limited to the type of method used for detecting the antibodies. Thus, in one embodiment, detecting comprises an assay selected from one or more of enzyme-linked immunosorbant assay (ELISA), enzyme-linked immunosorbant spot assay (ELISpot), radioimmunoassay, immunoradiometric assay, gel diffusion precipitation assay, immunodiffusion assay, in situ immunoassay, Western blot, precipitation reactions, gel agglutination assay, hemagglutination assay, complement fixation assay, immunofluorescence assay, protein A assay, and immunoelectrophoresis assay.

The invention's methods may further comprise administering a vaccine against *Neisseria meningitidis* to the subject, administering a booster dose of a vaccine against *Neisseria meningitidis* to the subject, and/or determining bactericidal activity against *Neisseria meningitidis* in a biological sample from the subject.

The subject that may be tested using the invention's methods may be a subject not infected with *Neisseria meningitidis*, a subject infected with *Neisseria meningitidis*, a subject vaccinated with a vaccine against *Neisseria meningitidis*, or a subject not vaccinated with a vaccine against *Neisseria meningitidis*.

The invention is not intended to be limited to the type or source of the biological sample. In one embodiment, the biological sample is exemplified by serum, blood, saliva, and urine.

The invention further provides kits comprising a reagent for detecting the presence of an antibody that specifically binds to a *Neisseria meningitidis* polypeptide selected from one or more of a) H.8, b) antigenic portion of H.8, c) Laz, and d) antigenic portion of Laz. In one embodiment, the kit further comprises instructions for using the kit.

Additionally provided herein are vaccines against *Neisseria meningitidis* comprising a mutant *Neisseria meningitidis* polypeptide selected from one or more of a) H.8, b) antigenic portion of H.8, c) Laz, and d) antigenic portion of Laz, wherein the mutant *Neisseria meningitidis* polypeptide is not antigenic. The invention is not limited to the type or method of producing the vaccine. Thus, the vaccine may comprise a *Neisseria meningitidis* polysaccharide and/or a *Neisseria meningitidis* membrane protein. In addition, it is not intended the invention be limited to a particular *Neisseria meningitidis* but rather expressly includes any serogroup, as exemplified by serogroup A, B, C, D, 29E, H, I, K, L, W-135, X, Y, and Z.

The invention's vaccines are not intended to be limited to the type of immune response that they elicit in a subject. In one embodiment, the vaccine elicits antibodies that specifically bind to a *Neisseria meningitidis* polypeptide other than a *Neisseria meningitidis* polypeptide selected from one or more of a) H.8, b) antigenic portion of H.8, c) Laz, and d) antigenic portion of Laz.

The invention also provides methods for producing a vaccine, comprising a) providing *Neisseria meningitidis* that comprises a mutation in a *Neisseria meningitidis* polypeptide selected from one or more of a) H.8, b) antigenic portion of H.8, c) Laz, and d) antigenic portion of Laz, and b) using the *Neisseria meningitidis* to prepare a vaccine comprising a *Neisseria meningitidis* protein. The mutation may include one or more deletion; insertion, and/or substitution.

The invention also provides methods for immunizing a mammalian subject, comprising a) providing i) any vaccine as described herein, and ii) a mammalian subject, and b) administering an immunologically effective amount of the vaccine to the subject to produce an immune response. In one embodiment, immune response comprises antibody that specifically binds to *Neisseria meningitidis* polypeptide selected from one or more of a) H.8, b) antigenic portion of H.8, c) Laz, and d) antigenic portion of Laz. In another embodiment, the immune response comprises T lymphocytes that specifically bind to *Neisseria meningitidis* polypeptide selected from one or more of a) H.8, b) antigenic portion of H.8, c) Laz, and d) antigenic portion of Laz.

The invention provides a method for identifying a mammalian subject at risk for infection by *Neisseria meningitidis*, comprising a) providing a biological sample from the subject, and b) detecting in the biological sample a *Neisseria meningitidis* blocking antibody that specifically binds to a *Neisseria meningitidis* polypeptide selected from the group of i) H.8, ii) antigenic portion of H.8, iii) Laz, and iv) antigenic portion of Laz. While it is not intended that H.8 be restricted to a particular source and/or sequence, in one embodiment, the H.8 that specifically binds to the *Neisseria meningitidis* blocking antibody is selected from the group of (a) sequence from amino acid 18 to 98 of SEQ ID NO:1, (b) sequence from amino acid 18 to 93 of SEQ ID NO:2, (c) sequence from amino acid 18 to 98 of SEQ ID NO:3, and (d) sequence from amino acid 18 to 88 of SEQ ID NO:4 (FIG. 13). It is also not intended that the invention be limited to a particular sequence of the antigenic portion of H.8. Nonetheless, in one embodiment, the portion of H.8 that specifically binds to the *Neisseria meningitidis* blocking antibody comprises at least one repeat of AAEAP (SEQ ID NO:10). In a further embodiment, the portion of H.8 comprises from 2 to 16 AAEAP (SEQ ID NO:10) sequences, as exemplified by having from 2 to 3, from 2 to 4, from 2 to 5, from 2 to 6, from 2 to 7, from 2 to 8, from 2 to 9, from 2 to 10, from 2 to 11, from 2 to 12, from 2 to 13, from 2 to 14, and from 2 to 15, AAEAP sequences (FIG. 13). It is contemplated that the source and/or sequence of Laz not be restricted. In one embodiment, Laz that specifically binds to the *Neisseria meningitidis* blocking antibody is selected from the group of (a) sequence from amino acid 18 to 61 of SEQ ID NO:5, (b) sequence from amino acid 18 to 61 of SEQ ID NO:6, (c) sequence from amino acid 18 to 61 of SEQ ID NO:7, (d) sequence from amino acid 18 to 60 of SEQ ID NO:8, and (e) sequence from amino acid 18 to 61 of SEQ ID NO:9 (FIG. 13). The invention is not limited to the type and/or source of the Laz portion. In one embodiment, the portion of Laz that specifically binds to the *Neisseria meningitidis* blocking antibody comprises at least one repeat of AAEAP (SEQ ID NO:10). In a particular embodiment, the portion of Laz comprises from 2 to 8 AAEAP (SEQ ID NO:10) sequences, including from 2 to 3, from 2 to 4, from 2 to 5, from 2 to 6 and from 2 to 7, AAEAP sequences. While the type of antibody is not limited to a particular type, in one embodiment, the blocking antibody is an IgG antibody. Data herein demonstrate that blocking was mediated by IgG (Example 2). In one embodiment, at least one of the antigenic portion of H.8 and the antigenic portion of Laz contains one or more amino acid that is conserved in *Neisseria meningitidis* H.8 and *Neisseria meningitidis* Laz. In another embodiment, at least one of the antigenic portion of H.8 and the antigenic portion of Laz contains one or more amino acid sequence AAEAP (SEQ ID NO:10). In a further embodiment, the level of the antibody that specifically binds to H.8 in the subject is higher than the level of the antibody in a subject that has not been infected with *Neisseria meningitidis* and has not been vaccinated against *Neisseria meningitidis*. In yet another embodiment, the level of the antibody that specifically binds to Laz in the subject is higher than the level of the antibody in a subject that has not been infected with *Neisseria meningitidis* and has not been vaccinated against *Neisseria meningitidis*. Also contemplated is that the level of the antibody that specifically binds to the antigenic portion of H.8 in the subject is higher than the level of the antibody in a subject that has not been infected with *Neisseria meningitidis* and has not been vaccinated against Neisseria meningitidis. In another example, the level of the antibody that specifically binds to the antigenic portion of Laz in the subject is higher than the level of the antibody in a subject that has not been infected with Neisseria meningitidis and has not been vaccinated against Neisseria meningitidis. In yet a further illustration, the detecting comprises an assay selected from the group of enzyme-linked immunosorbant assay (ELISA) and enzyme-linked immunosorbant spot (ELISpot) assay. In another embodiment, the method further comprises c) administering a vaccine against Neisseria meningitidis to the subject. In an alternative embodiment, the method further comprises c) administering a booster dose of a vaccine against Neisseria meningitidis to the subject. In a further alternative, the method further comprises c) determining Neisseria meningitidis bactericidal antibody activity against Neisseria meningitidis in a biological sample from the subject. In one example, the biological sample is selected from the group of serum, blood, saliva, and urine.

The invention also provides a kit comprising a reagent for detecting the presence of a Neisseria meningitidis blocking antibody that specifically binds to a Neisseria meningitidis polypeptide selected from the group of a) H.8, b) antigenic portion of H.8, c) Laz, and d) antigenic portion of Laz. In one embodiment, the kit further comprises instructions for using the kit. Without limiting the source and/or sequence of H.8, in one embodiment, H.8 that specifically binds to the Neisseria meningitidis blocking antibody is selected from the group of (a) sequence from amino acid 18 to 98 of SEQ ID NO:1, (b) sequence from amino acid 18 to 93 of SEQ ID NO:2, (c) sequence from amino acid 18 to 98 of SEQ ID NO:3, and (d) sequence from amino acid 18 to 88 of SEQ ID NO:4. Also without restricting the source and/or sequence of the portion of H.8, in one embodiment, the portion of H.8 that specifically binds to the Neisseria meningitidis blocking antibody comprises at least one repeat of AAEAP (SEQ ID NO:10). Without limiting the source and/or sequence of Laz, in one embodiment, Laz that specifically binds to the Neisseria meningitidis blocking antibody is selected from the group of (a) sequence from amino acid 18 to 61 of SEQ ID NO:5, (b) sequence from amino acid 18 to 61 of SEQ ID NO:6, (c) sequence from amino acid 18 to 61 of SEQ ID NO:7, (d) sequence from amino acid 18 to 60 of SEQ ID NO:8, and (e) sequence from amino acid 18 to 61 of SEQ ID NO:9. Without limiting the source and/or sequence of the antigenic portion of Laz, in one embodiment, the portion of Laz that specifically binds to the Neisseria meningitidis blocking antibody comprises at least one repeat of AAEAP (SEQ ID NO:10). In a further embodiment, the reagent comprises an antibody that specifically binds to the Neisseria meningitidis blocking antibody.

The invention also provides a kit comprising a reagent for detecting the presence of a Neisseria meningitidis bactericidal antibody that specifically binds to a Neisseria meningitidis polypeptide selected from the group of a) antigenic portion of H.8 that reduces Neisseria meningitidis blocking antibody activity, b) Laz azurin domain, and c) antigenic portion of Laz azurin domain. The term "reduces Neisseria meningitidis blocking antibody activity" means reduce the level of specific binding of the blocking antibody to its antigen.

The invention also provides a mutant Neisseria meningitidis that lacks a polypeptide sequence that specifically binds to a Neisseria meningitidis blocking antibody, wherein the polypeptide sequence is selected from the group of a) H.8, b) portion of H.8, and c) portion of Laz. These mutants may be generated using methods known in the art, e.g., methods for making knockout mutant bacteria. Without limiting the source and/or sequence of H.8, in one embodiment, H.8 that specifically binds to Neisseria meningitidis blocking antibody is selected from the group of (a) sequence from amino acid 18 to 98 of SEQ ID NO:1, (b) sequence from amino acid 18 to 93 of SEQ ID NO:2, (c) sequence from amino acid 18 to 98 of SEQ ID NO:3, and (d) sequence from amino acid 18 to 88 of SEQ ID NO:4. Without limiting the source and/or sequence of the portion of H.8, in one embodiment, the portion of H.8 that specifically binds to a Neisseria meningitidis blocking antibody comprises at least one repeat of AAEAP (SEQ ID NO:10). In a particular embodiment, the portion of H.8 comprises from 2 to 16 AAEAP (SEQ ID NO:10) sequences. Without limiting the source and/or sequence of the portion of Laz, in one embodiment, the portion of Laz that specifically binds to Neisseria meningitidis blocking antibody is selected from the group of (a) sequence from amino acid 18 to 61 of SEQ ID NO:5, (b) sequence from amino acid 18 to 61 of SEQ ID NO:6, (c) sequence from amino acid 18 to 61 of SEQ ID NO:7, (d) sequence from amino acid 18 to 60 of SEQ ID NO:8, and (e) sequence from amino acid 18 to 61 of SEQ ID NO:9. In a further embodiment, the portion of Laz that specifically binds to Neisseria meningitidis blocking antibody comprises at least one repeat of AAEAP (SEQ ID NO:10). In a particular embodiment, the portion of Laz comprises from 2 to 8 AAEAP (SEQ ID NO:10) sequences.

The invention also provides a vaccine against Neisseria meningitidis produced by a method comprising providing an outer membrane vesicle (OMV) from any of the mutant Neisseria meningitidis described herein. In one embodiment, the outer membrane vesicle is purified. Methods for purifying Neisseria meningitidis, OMVs are known in the art (Wedege et al. Clin Vaccine Immunol. 2007; 14(7):830-8).

The invention's vaccines may further comprise an antigenic Neisseria meningitidis polypeptide that specifically binds to a Neisseria meningitidis bactericidal antibody. For example, the antigenic. Neisseria meningitidis polypeptide that specifically binds to Neisseria meningitidis bactericidal antibody comprises a Laz azurin domain. In a particular embodiment, the Laz azurin domain is selected from amino acid 62 to 183 of at least one of SEQ ID NOs:5-7 and 9, and from amino acids 61 to 183 of SEQ ID NO:8. In another embodiment, the Neisseria meningitidis polypeptide that specifically binds to Neisseria meningitidis bactericidal antibody is selected from the group of GNA2132, GNA1030, GNA2091, GNA1870 and NadA. These five antigens were described in Giuliani et al. (2006) 103:10834-10839. In a further embodiment, the Neisseria meningitidis polypeptide that specifically binds to Neisseria meningitidis bactericidal antibody is selected from the group of PorA molecules P1.7, P1.2, P1.4. The bactericidal activity of these monoclonal antibodies was previously described (Welsch et al. J Infect Dis. 2008 Apr. 1; 197(7):1053-61).

The invention's vaccines may further comprise an antigenic portion of Neisseria meningitidis polypeptide H.8, wherein the portion reduces Neisseria meningitidis blocking antibody activity. Data herein (Example 3) demonstrate that the exemplary Lip C30 and Lip N30 sequences elicit antibodies that restore bacterial killing by blocking the Neisseria meningitidis blocking antibody (i.e., by reducing the Neisseria meningitidis blocking antibody activity). These sequences are useful for increasing the efficacy (i.e., increasing the bactericidal antibody activity against Neisseria meningitidis) of vaccines (including non-lipidated polypeptide vaccines, lipidated polypeptide vaccines, outer membrane vesicle vaccine, and/or polysaccharide vaccines) that elicit *Neisseria meningitidis* bactericidal antibodies. Thus, in one embodiment, the H.8 portion that reduces *Neisseria meningitidis* blocking antibody activity comprises a H.8 C-terminal 30-amino acid sequence selected from amino acid 69 to 98 of at least one of SEQ ID NO:1, SEQ ID NO:2, SEQ ID NO:3 and SEQ ID NO:4. In an alternative embodiment, the H.8 portion that reduces *Neisseria meningitidis* blocking antibody activity comprises a H.8 N-terminal 30-amino acid sequence selected from amino acid 18 to 47 of at least one of SEQ ID NO:1, SEQ ID NO:2, SEQ ID NO:3 and SEQ ID NO:4.

The invention also provides a vaccine against *Neisseria meningitidis* comprising an antigenic polypeptide selected from the group of a) *Neisseria meningitidis* Laz azurin domain that specifically binds to *Neisseria meningitidis* bactericidal antibody, and b) portion of *Neisseria meningitidis* polypeptide H.8; wherein the portion reduces *Neisseria meningitidis* blocking antibody activity. Without limiting the source and/or sequence of the Laz azurin domain, in one embodiment, the Laz azurin domain that specifically binds to *Neisseria meningitidis* bactericidal antibody is selected from amino acid 62 to 183 of at least one of SEQ ID NOs:5-7 and 9, and from amino acids 61 to 183 of SEQ ID NO:8. Without limiting the source and/or sequence of the H.8 portion, in one embodiment, the H.8 portion that reduces *Neisseria meningitidis* blocking antibody activity comprises a H.8 C-terminal 30-amino acid sequence selected from amino acid 69 to 98 of at least one of SEQ ID NO:1, SEQ ID NO:2, SEQ ID NO:3 and SEQ ID NO:4. In another embodiment, the H.8 portion that reduces *Neisseria meningitidis* blocking antibody activity comprises a H.8 N-terminal 30-amino acid sequence selected from amino acid 18 to 47 of at least one of SEQ ID NO:1, SEQ ID NO:2, SEQ ID NO:3 and SEQ ID NO:4.

Any of the invention's sequences (such as H.8, portions of H.8, Laz, portions of Laz) may further contain a terminal cysteine residue selected from the group of cysteine residue is at the N-terminal end of the antigenic polypeptide, and cysteine residue is at the C-terminal end of the antigenic polypeptide. Adding a N-terminal Cys may be useful in, for example, linking the sequences of the invention to a solid support, in order to purify antibody that binds specifically to the invention's sequences. Thus, in one embodiment, the Lip C30 sequence may further contain an additional N-terminal Cys residue (italicized and underlined in the following SEQ ID NO:11: *C*AEAAATEAPAAEAAATEAPAAEAPAAE-AAK). In another embodiment, the Lip N30 sequence may further contain an additional N-terminal Cys residue (italicized and underlined in the following SEQ ID NO:12: *C*CGGEKAAEAPAAEAPAAEAPATEAPAAEAP.

In one embodiment, any of the vaccines of the invention may lack a *Neisseria meningitidis* polypeptide sequence that specifically binds to a *Neisseria meningitidis* blocking antibody, wherein the polypeptide sequence is selected from the group of i) H.8, ii) portion of H.8, and iii) portion of Laz. Without limiting the source and/or sequence of H.8, in one embodiment of the invention's vaccines, the H.8 that specifically binds to *Neisseria meningitidis* blocking antibody is selected from the group of (a) sequence from amino acid 18 to 98 of SEQ ID NO:1, (b) sequence from amino acid 18 to 93 of SEQ ID NO:2, (c) sequence from amino acid 18 to 98 of SEQ ID NO:3, and (d) sequence from amino acid 18 to 88 of SEQ ID NO:4. Without limiting the source and/or sequence of the H.8 portion, in one embodiment of the invention's vaccines, the portion of H.8 that specifically binds to a *Neisseria meningitidis* blocking antibody comprises at least one repeat of AAEAP (SEQ ID NO:10). Without limiting the source and/or sequence of the portion of Laz, in one embodiment, the portion of Laz that specifically binds to *Neisseria meningitidis* blocking antibody is selected from the group of (a) sequence from amino acid 18 to 61 of SEQ ID NO:5, (b) sequence from amino acid 18 to 61 of SEQ ID NO:6, (c) sequence from amino acid 18 to 61 of SEQ ID NO:7, (d) sequence from amino acid 18 to 60 of SEQ ID NO:8, and (e) sequence from amino acid 18 to 61 of SEQ ID NO:9. In a particular embodiment, the portion of Laz that specifically binds to *Neisseria meningitidis* blocking antibody comprises at least one repeat of AAEAP (SEQ ID NO:10). More particularly, the portion of Laz may comprise from 2 to 8 AAEAP (SEQ ID NO:10) sequences, including from 2 to 3, from 2 to 4, from 2 to 5, from 2 to 6 and from 2 to 7, AAEAP sequences.

In one embodiment, any of the vaccines of the invention may comprise a *Neisseria meningitidis* polysaccharide and/or a *Neisseria meningitidis* membrane protein and/or a *Neisseria meningitidis* outer membrane vesicle. In one embodiment, the *Neisseria meningitidis* used in any of the invention's compositions and/or methods is exemplified by serogroup A, B, C, D, 29E, H, I, K, L, W-135, X, Y, and Z.

The invention also provides a method for producing a *Neisseria meningitidis* vaccine, comprising a) providing an expression vector that comprises a recombinant nucleotide sequence that encodes a H.8 portion, wherein the H.8 portion reduces *Neisseria meningitidis* blocking antibody activity, and wherein the H.8 portion is selected from the group of i) an amino acid sequence selected from amino acid 69 to 98 of at least one of SEQ ID NO:1, SEQ ID NO:2, SEQ ID NO:3 and SEQ ID NO:4, and ii) an amino acid sequence selected from amino acid 18 to 47 of at least one of SEQ ID NO:1, SEQ ID NO:2, SEQ ID NO:3 and SEQ ID NO:4, and b) introducing the vector into a cell under conditions suitable for expression of the H.8 portion. In one embodiment, the method further comprises c) purifying the expressed H.8 portion. In another embodiment, the recombinant nucleotide sequence lacks a nucleic acid sequence that encodes a polypeptide sequence that specifically binds to a *Neisseria meningitidis* blocking antibody, wherein the polypeptide sequence is selected from the group of i) H.8, ii) portion of H.8, and iii) portion of Laz. Without limiting the source and/or sequence of H.8, in one embodiment, the H.8 that specifically binds to *Neisseria meningitidis* blocking antibody is selected from the group of (a) sequence from amino acid 18 to 98 of SEQ ID NO:1, (b) sequence from amino acid 18 to 93 of SEQ ID NO:2, (c) sequence from amino acid 18 to 98 of SEQ ID NO:3, and (d) sequence from amino acid 18 to 88 of SEQ ID NO:4. Without limiting the source and/or sequence of the portion of H.8, in one embodiment, the portion of H.8 that specifically binds to a *Neisseria meningitidis* blocking antibody comprises at least one repeat of AAEAP (SEQ ID NO:10). In a particular embodiment, the portion of H.8 comprises from 2 to 16 AAEAP (SEQ ID NO:10) sequences. Without limiting the source and/or sequence of Laz, in one embodiment, Laz that specifically binds to *Neisseria meningitidis* blocking antibody is selected from the group of (a) sequence from amino acid 18 to 61 of SEQ ID NO:5, (b) sequence from amino acid 18 to 61 of SEQ ID NO:6, (c) sequence from amino acid 18 to 61 of SEQ ID NO:7, (d) sequence from amino acid 18 to 60 of SEQ ID NO:8, and (e) sequence from amino acid 18 to 61 of SEQ ID NO:9. Without limiting the source and/or sequence of the antigenic portion of Laz, in one embodiment, the portion of Laz that specifically binds to *Neisseria meningitidis* blocking antibody comprises at least one repeat of AAEAP (SEQ ID NO:10). In a particular embodiment, the portion of Laz comprises from 2 to 8 AAEAP (SEQ ID NO:10) sequences. In some embodiments, any of the expressed amino acid sequences of the invention may be comprised in a lipoprotein. This is useful in, for example, increasing the bactericidal activity of the invention's vaccines. Methods for such expression of *Neisseria meningitidis* proteins are known in the art, including cloning the gene to be expressed behind a lipoprotein signal sequence, such as the P4 lipoprotein signal sequence of *Haemophilus influenzae* (Fletcher et al. (2004) Infection and Immunity 72(4): 2088-2100).

The invention also provides a method for producing a *Neisseria meningitidis* vaccine, comprising a) providing an expression vector that comprises a recombinant nucleotide sequence that encodes a Laz azurin domain, wherein the Laz azurin domain reduces *Neisseria meningitidis* blocking antibody activity, and wherein the Laz azurin domain is selected from the group of amino acid 62 to 183 of at least one of SEQ ID NOs:5-7 and 9, and amino acids 61 to 183 of SEQ ID NO:8, and b) introducing the vector into a cell under conditions suitable for expression of the Laz azurin domain. In one embodiment, the method further comprises c) purifying the expressed Laz azurin domain. In another embodiment, the recombinant nucleotide sequence lacks a nucleic acid sequence that encodes a polypeptide sequence that specifically binds to a *Neisseria meningitidis* blocking antibody, wherein the polypeptide sequence is selected from the group of i) H.8, ii) portion of H.8, and iii) portion of Laz. In one embodiment, the expressed amino acid sequence is comprised in a lipoprotein.

Also provided by the invention is a method for producing a *Neisseria meningitidis* vaccine, comprising a) providing any of the mutant *Neisseria meningitidis* bacteria described herein, and b) preparing an outer membrane vesicle (OMV) from the mutant bacteria. In one embodiment, the method further comprises c) purifying the outer membrane vesicle.

The invention also provides a method for immunizing a mammalian subject, comprising a) providing i) any of the vaccines described herein, and ii) a mammalian subject, and b) administering an immunologically effective amount of the vaccine to the subject to produce an immune response. In one embodiment, the immune response comprises *Neisseria meningitidis* bactericidal antibody. In one embodiment, the method further comprises c) detecting the presence of *Neisseria meningitidis* bactericidal antibody.

Figure 1:
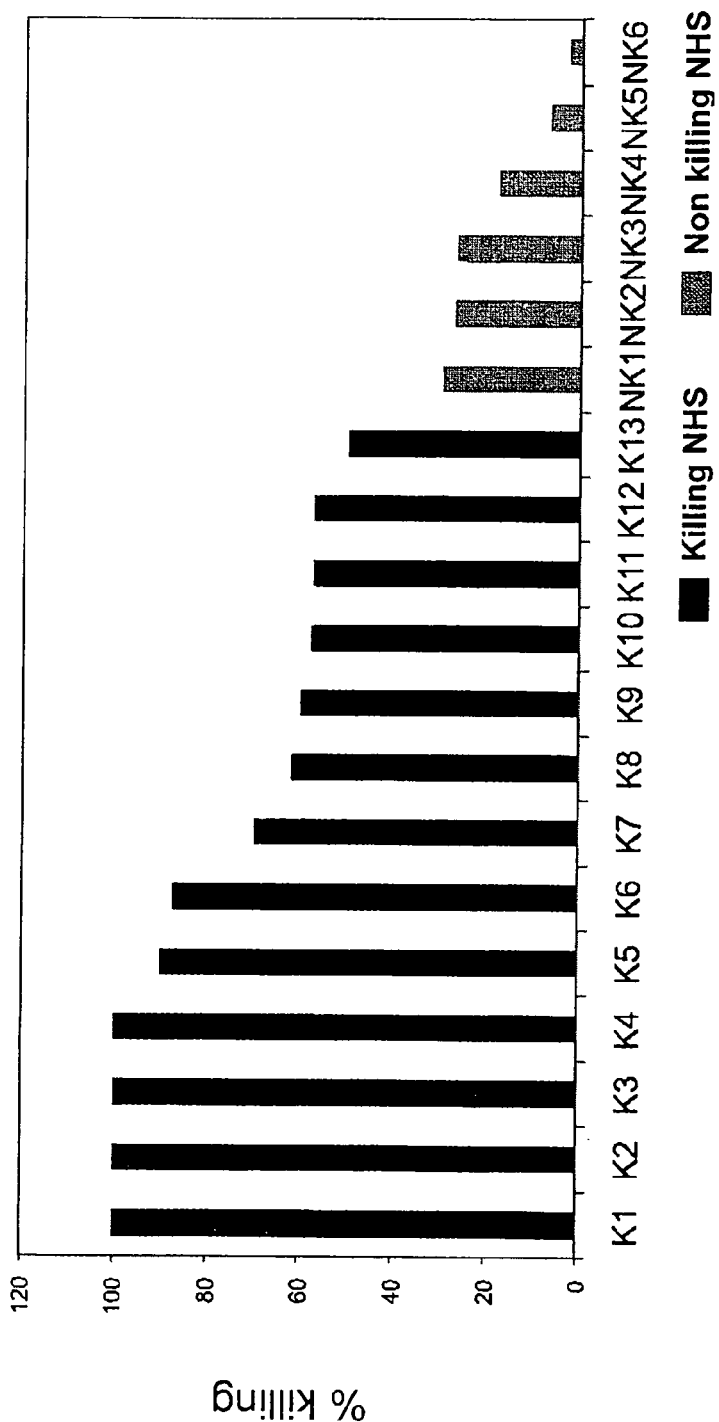
FIG. 1. Killing of serogroup B *Neisseria meningitidis* strain H44/76 by individual human sera. Serum isolated from 19 individuals was tested for their ability to kill wild-type strain H44/76 in a serum bactericidal assay. The concentration of serum in the reaction mixture was 10%. Serum that killed >50% of bacteria were designated 'killing serum' and those that killed <50% were called 'non killing serum'.
Figure 2:
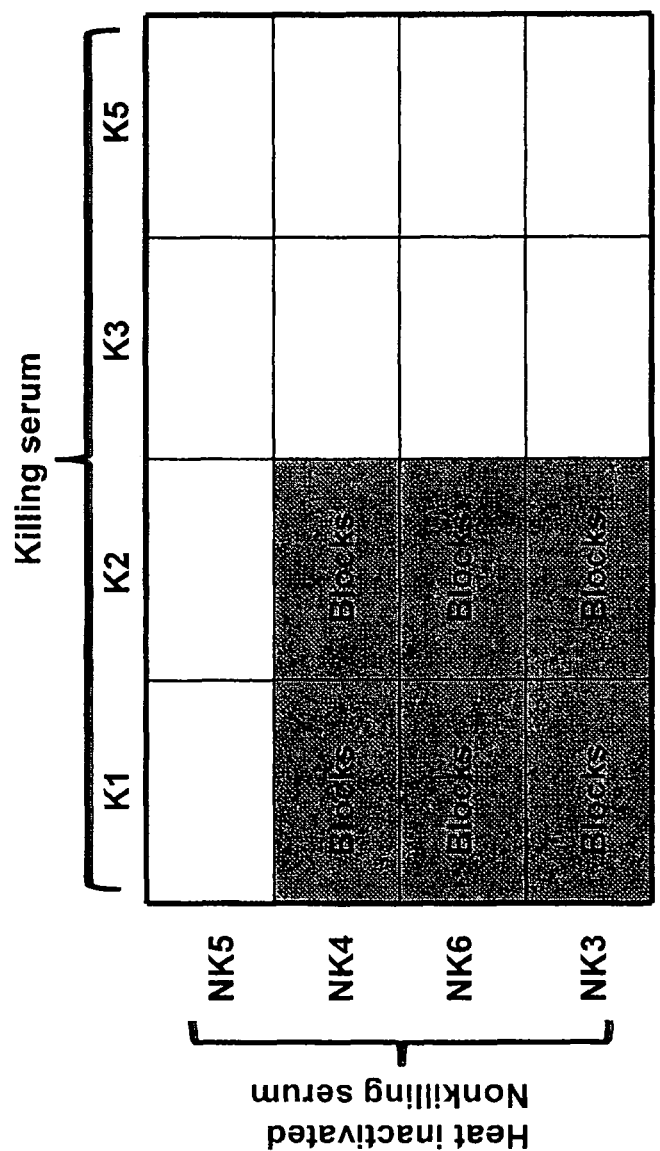
FIG. 2. Prevalence of blocking activity in normal human sera. The ability of four nonkilling sera was tested to block killing by each of four killing sera (sera were randomly selected). Three of the four nonkilling sera (heat-inactivated) were able to block killing by two of four killing sera. In this assay, the final concentration of heat-inactivated nonkilling serum in the reaction mixture was 20% and the concentration of the killing serum (complement active) was 10%. Blocking was defined as a ≥50% reduction in killing relative compared to bactericidal activity with killing serum alone. Green boxes indicate no increase in survival (i.e., no blocking). These data suggest that the antibody present in certain killing sera (for example, K3 and K5) can overcome the effects of blocking antibody present in NK4, NK6 and NK3).
Figure 3:
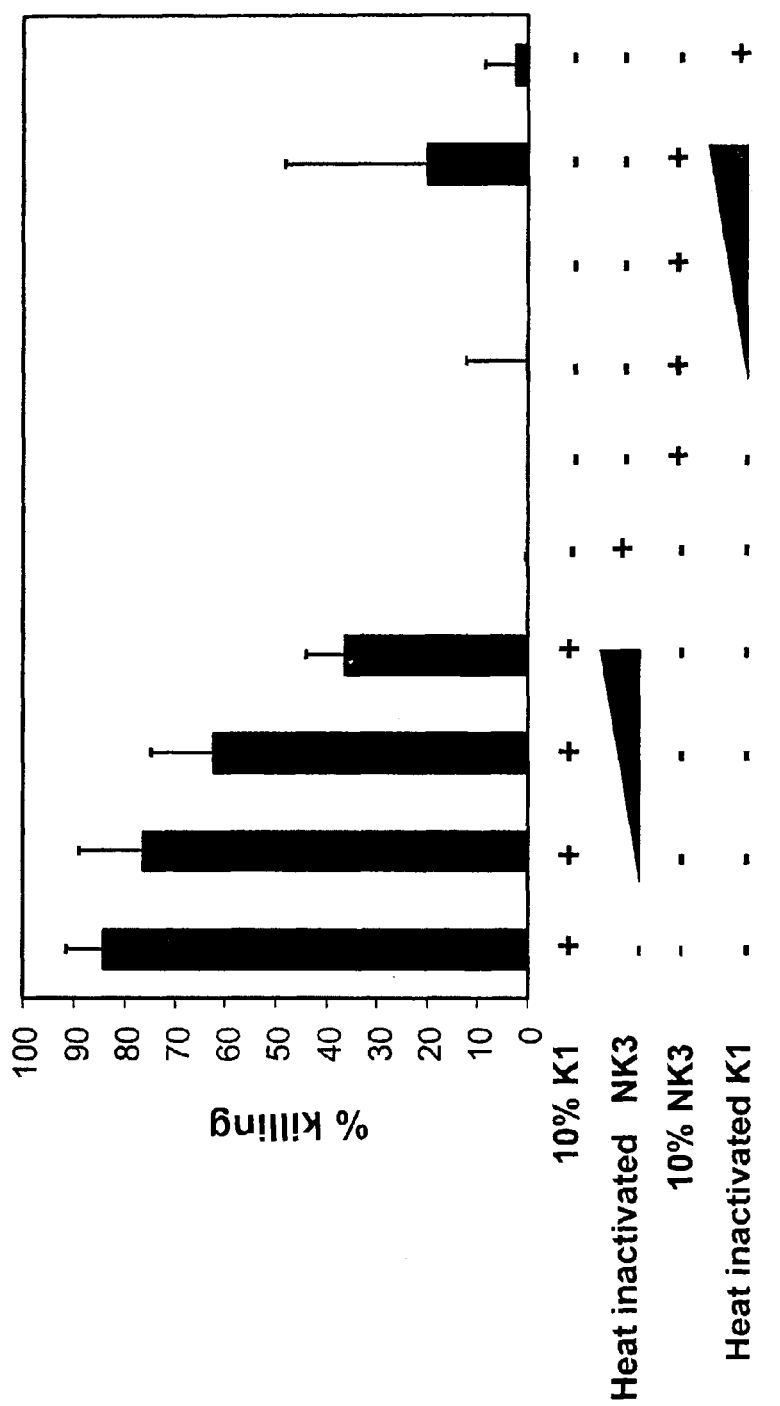
FIG. 3. Heat inactivated nonkilling serum NK3 blocks bactericidal activity of killing serum K1. A bactericidal assay was performed where wild type serogroup B strain H44/76 was incubated in 10% killing NHS K1 either in the absence, or the presence of increasing amounts (5%, 10% and 20%) of heat inactivated (56° C. for 30 min, to inactivate complement, but preserve antibody function) nonkilling serum NK3. In the converse experiment, 10% serum NK3 (complement active) was incubated with increasing amounts of heat inactivated serum K1.
Figure 4:
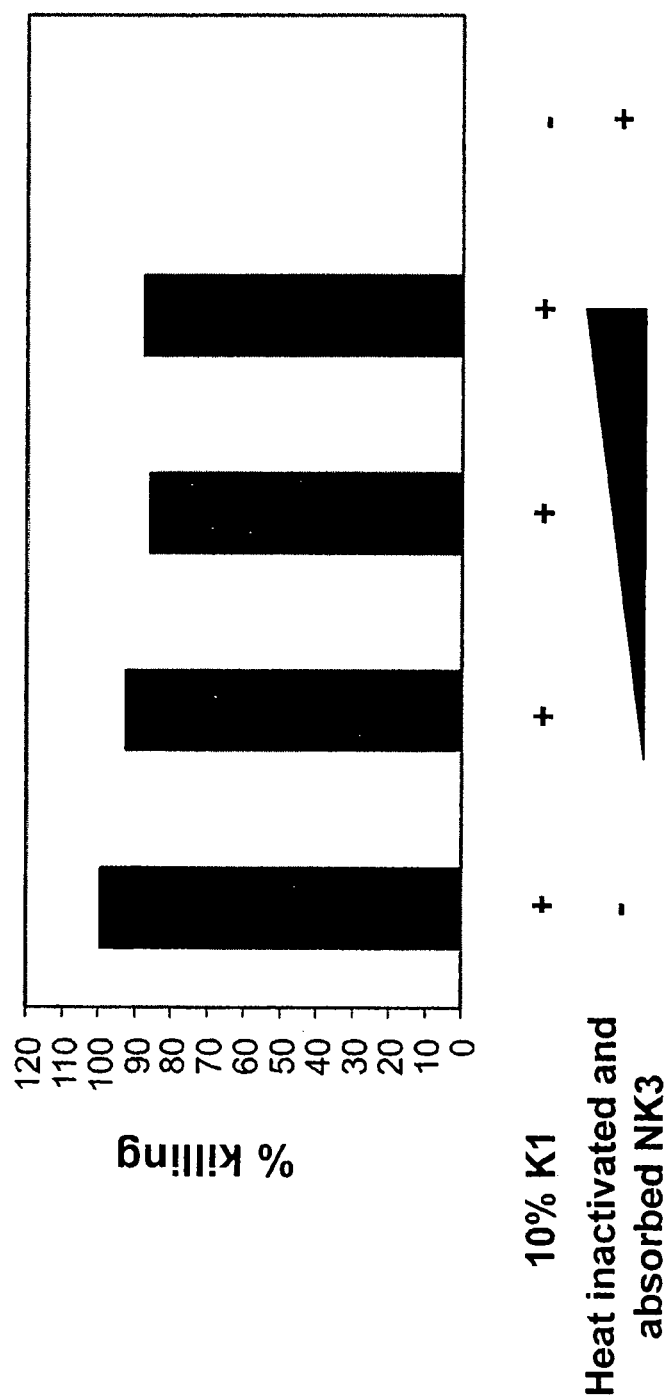
FIG. 4. IgG antibody in nonkilling serum NK3 is responsible for blocking of killing by serum K1. Nonkilling serum NK3 was depleted of IgG using the product protein G Separation-Pharmacia-Agarose column sold under the trademark protein G SEPHAROSE column followed by incubation with wild-type strain H44/76 to remove all *Neisseria meningitidis* serogroup B specific IgM. Strain H44/76 was incubated with killing serum K1 and increasing doses (5%, 10% and 20%) of the heat-inactivated absorbed blocking serum NK3 and bacterial survival was measured in a bactericidal assay.
Figure 5:
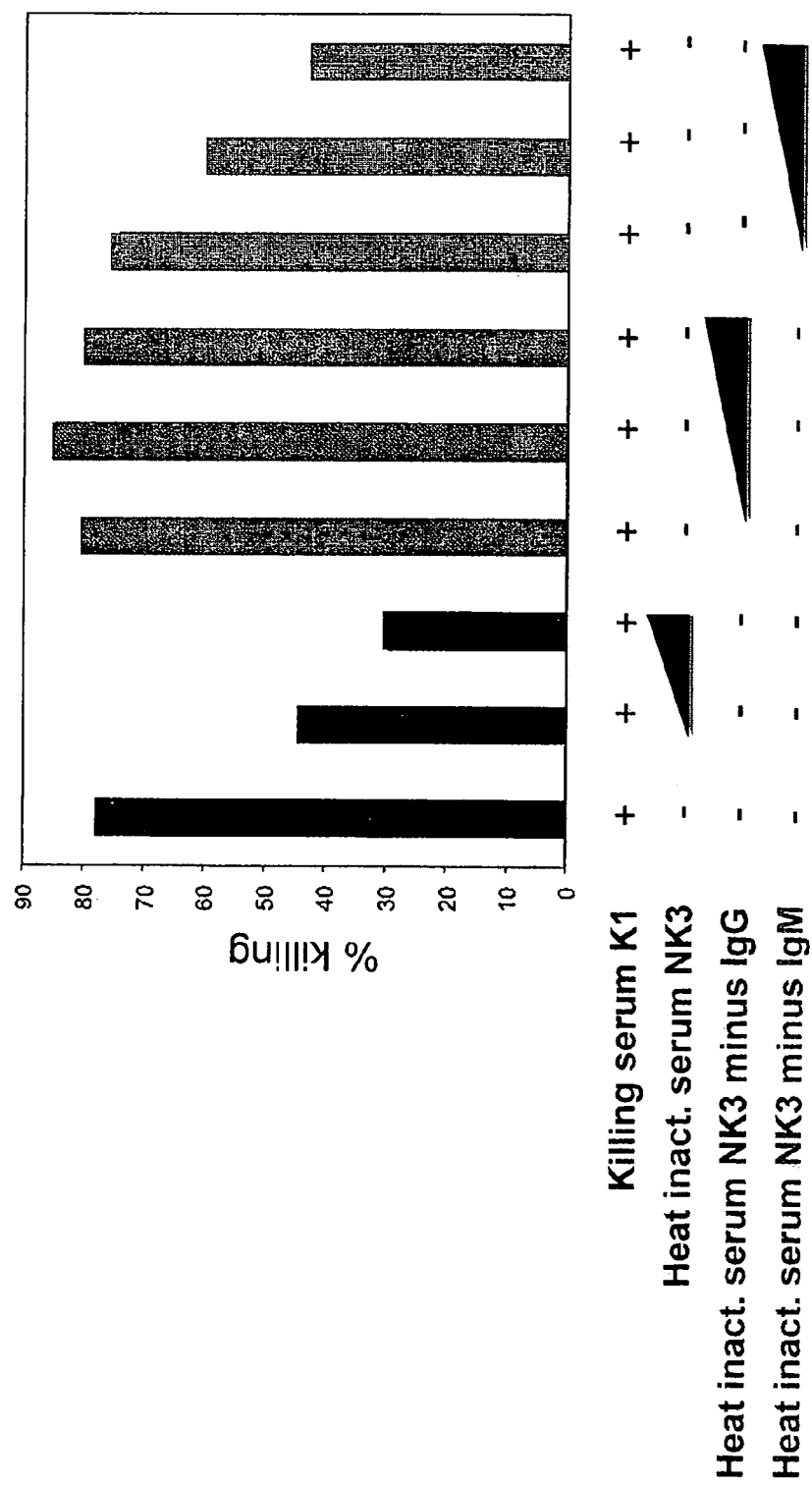
FIG. 5. Blocking serum IgG is mainly responsible for blocking bactericidal activity of killing serum. Blocking serum NK3 was depleted of IgG or IgM by passage over the product protein G Separation-Pharmacia-Agarose column sold under the trademark protein G SEPHAROSE column or mouse anti-human IgM agarose column, respectively. Strain H44/76 was incubated with killing serum K1 mixed with increasing doses (10% and 20%) heat inactivated NK3 (contains IgG and IgM), IgG-depleted NK3 or IgM-depleted NK3 and survival was measured in a serum bactericidal assay.
Figure 6:
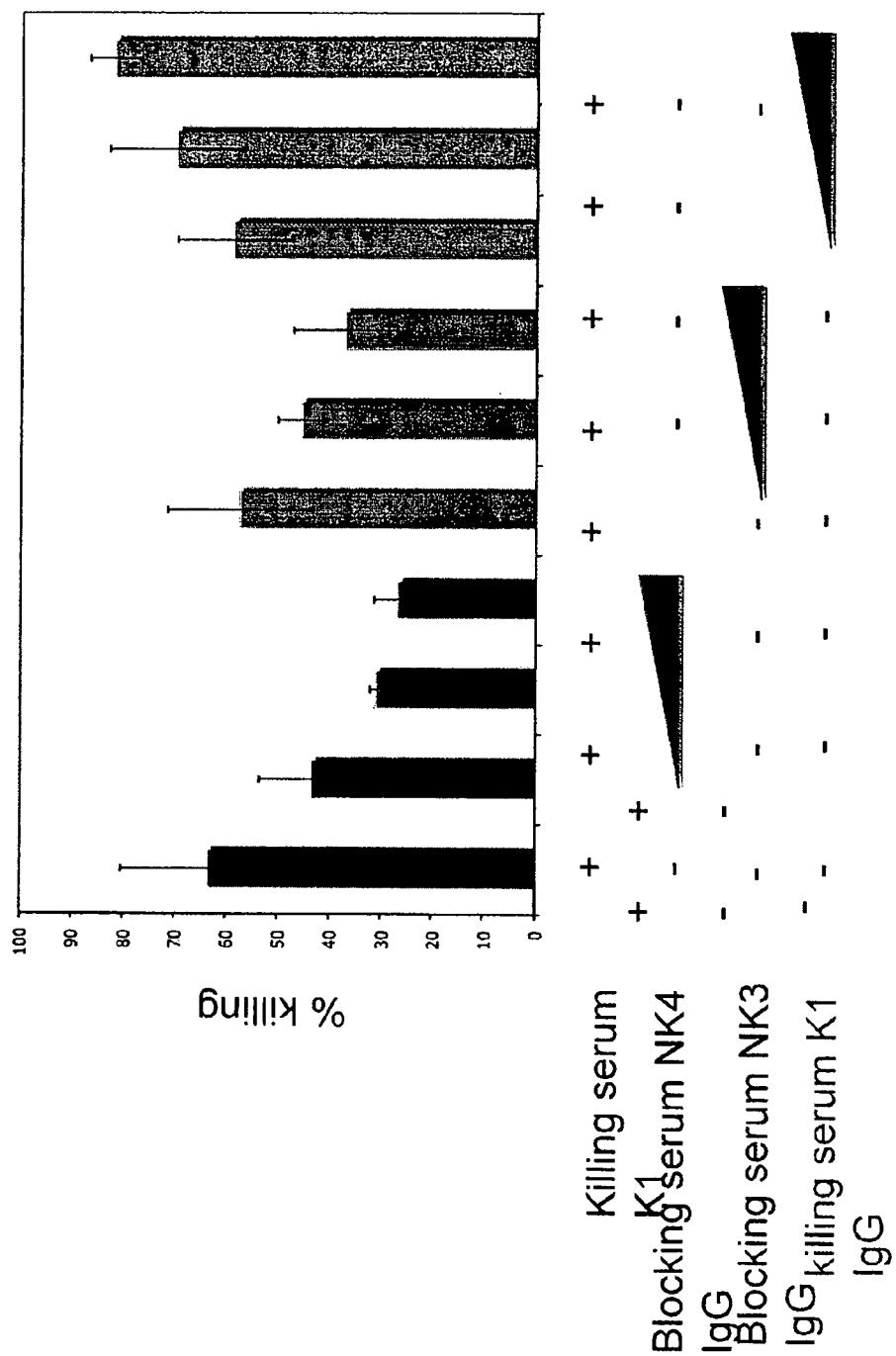
FIG. 6. IgG purified from blocking sera blocks bactericidal activity of killing serum. IgG was purified from blocking serum NK3, NK4 and killing serum K1 using the product protein G Separation-Pharmacia-Agarose column sold under the trademark protein G SEPHAROSE column. A bactericidal assay was performed with wild type H44/76 incubated with 10% killing serum K1 mixed with increasing doses of IgG (50, 100 and 200 µg) purified from sera NK3, NK4 and K1.
Figure 7:
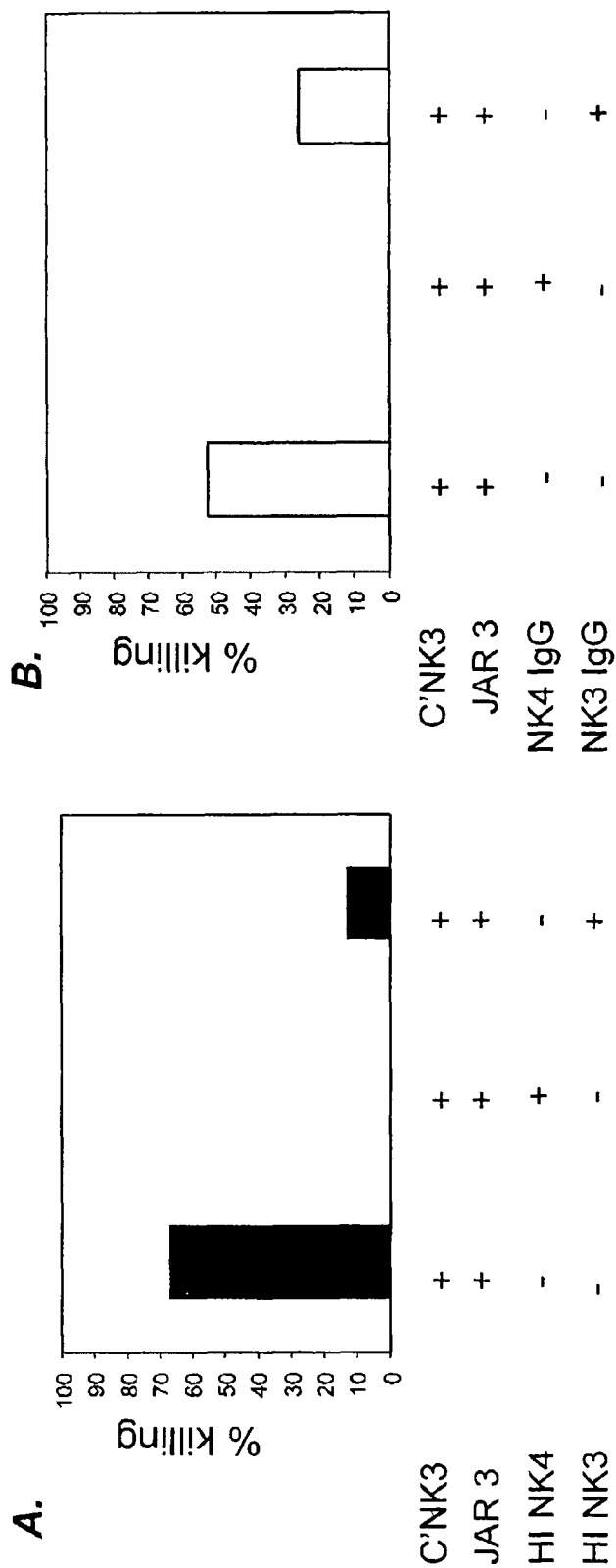
FIG. 7. Blocking of the bactericidal activity of monoclonal antibody JAR 3 against factor H binding protein (fHbp, also called GNA1870 or LP2086, a meningococcal protein vaccine candidate). A. Killing by JAR 3 is blocked by heat-inactivated blocking serum. Wild-type H44/76 was incubated with 0.3 µg/ml JAR 3 mixed with either 10% heat-inactivated blocking serum NK3 or NK4. The complement source (C'NK3) was prepared by depleting IgG and IgM from NK3 by sequential passage over the product protein G Separation-Pharmacia-Agarose column sold under the trademark Protein G SEPHAROSE and anti-human IgM agarose. B. Killing by JAR 3 is blocked by IgG derived from blocking sera. IgG purified from NK3 and NK4 both reduce killing by JAR 3.
Figure 8:
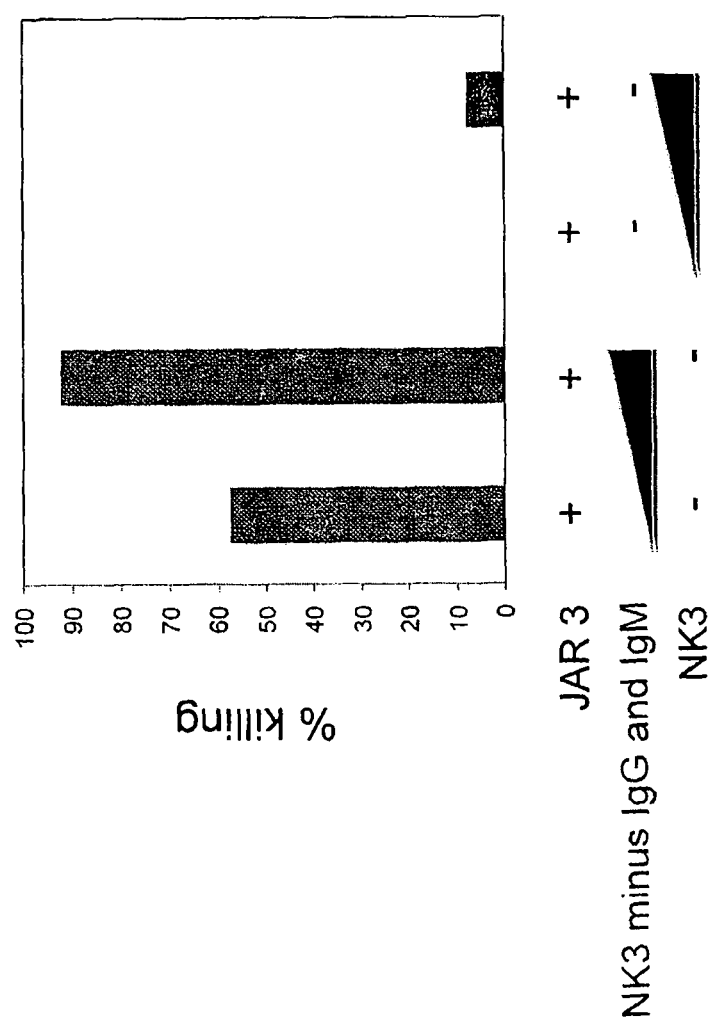
FIG. 8. Anti-fHbp monoclonal does not effect killing in the presence of blocking IgG. A bactericidal assay was where serogroup B H44/76 was incubated with 0.3 µg/ml JAR 3 mixed with increasing amounts (20% and 40%) of serum NK3 from which IgG and IgM was depleted (NK3 minus IgG and IgM), or serum NK3 (Ab intact). Killing by JAR 3 occurred only when (endogenous) antibody was depleted from NK3; presence of the native (or endogenous) NK3 antibody blocked killing by JAR 3.
Figure 9:
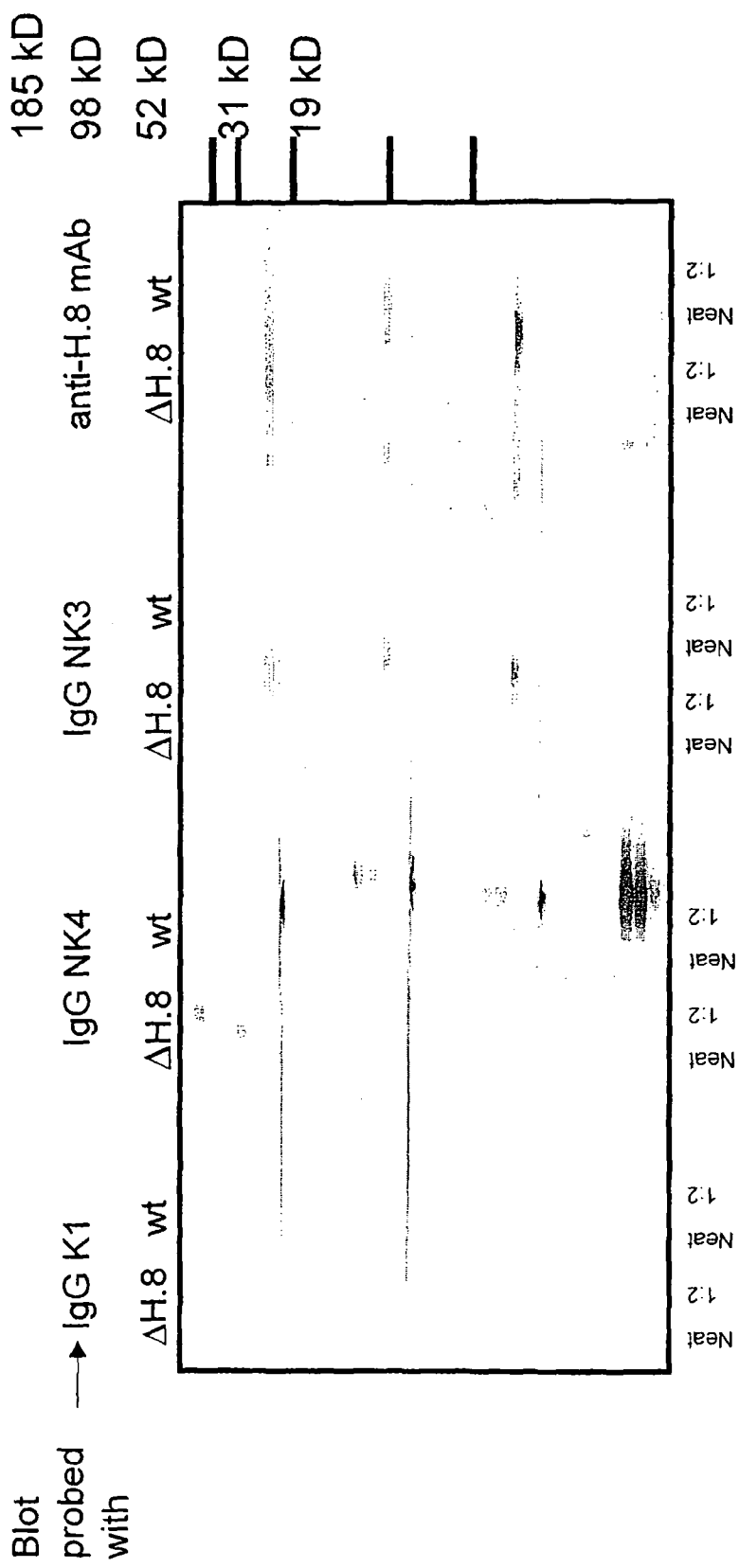

FIG. 9. Blocking sera contain antibody directed against lipoprotein H.8. Whole cell lysates of strain H44/76 and its isogenic lipoprotein H.8 knockout mutant were electrophoresed on a 12% Bis-tris gel followed by western blotting. Two doses of bacterial lysates (labeled 'neat' and '1:2') were tested. Blots were incubated with IgG purified from killing serum K1 and blocking sera NK3 and NK4. Human IgG-reactive bands were disclosed with alkaline phosphatase conjugated anti-human IgG. Parallel lanes were stained with an anti-H.8 mAb. IgG from blocking sera showed reactivity at ~19 kD (indicated by the arrow) at a location that corresponded to the migration of H.8.

Figure 10:
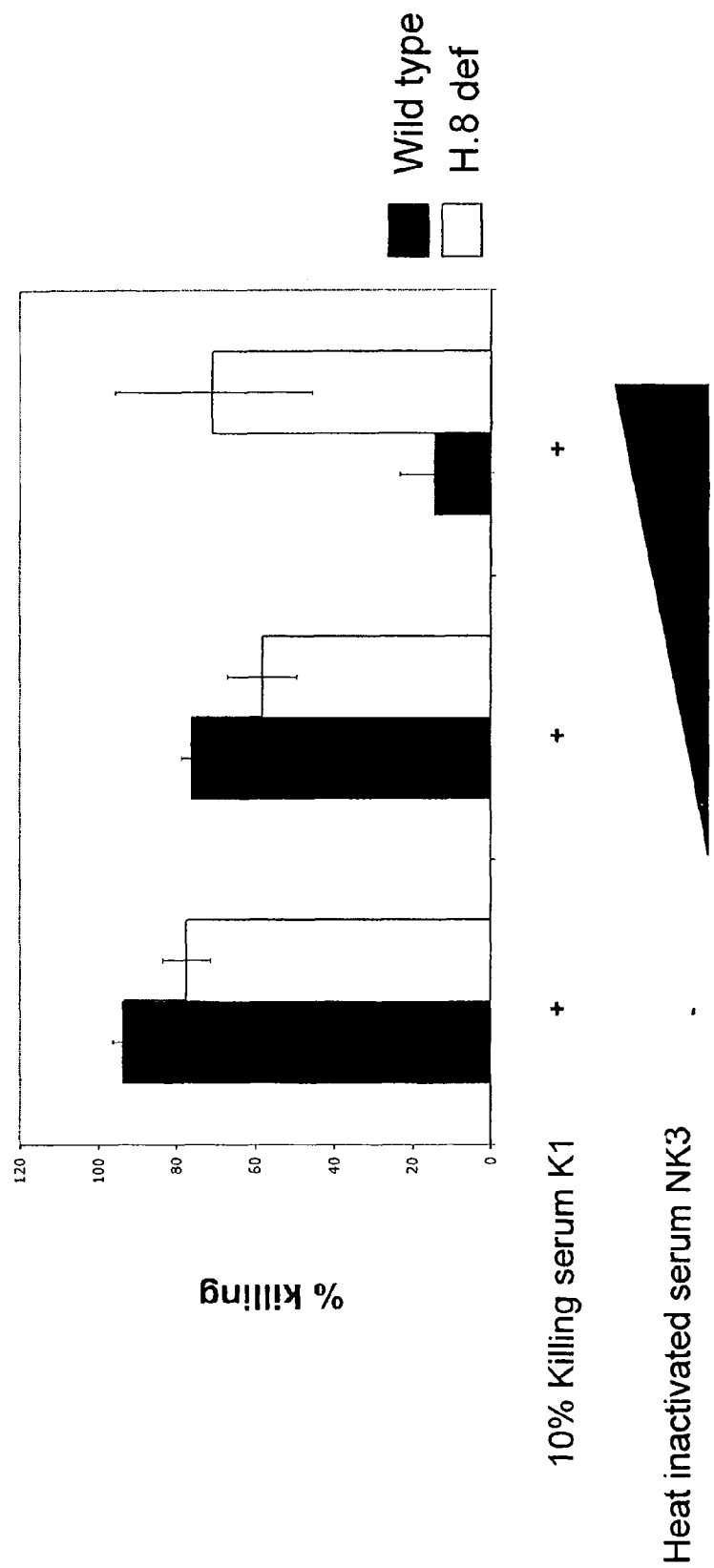

FIG. 10. Loss of H.8 abrogates blocking. Wild type strain H44/76 and its isogenic H8 (Lip) deficient mutant were incubated with 10% killing serum K1 and increasing doses (10% and 20%) heat inactivated blocking serum NK3 and survival was measured in a serum bactericidal assay. While the addition of heat-inactivated NK3 resulted in decreased killing (blocking) of the wild-type strain, no blocking was observed with the H.8 deletion mutant.

FIG. 11. Alignment of Lip (H.8) and Laz proteins, including signal polypeptide (also known as leader polypeptide) sequences that are lacking from the mature Lip and Laz proteins, from different strains of *Neisseria*. H.8: MC58—Lip/H.8, orf NMB 1523, NP_274531, annotated as hypothetical protein (SEQ ID NO:1); Z2491—Lip/H.8, orf not in GenBank (SEQ ID NO:3); FAM18—Lip/H.8, orf not in GenBank (SEQ ID NO:2); FA1090—Lip/H.8, orf NGO0983, YP_208081.1 (SEQ ID NO:4). Laz: MC58—Laz, orf NMB 1533 NP_274540.1, mis-annotated in GenBank as H.8 (SEQ ID NO:5); Z2491—Laz, orf, NMA1733, NP_284448.1, mis-annotated in GenBank as H.8 (SEQ ID NO:7); FAM18—Laz, orf NMC1462, YP_975449.1, mis-annotated in GenBank as H.8, alternate start codon annotated (MHFDFCKTEYYFIDWRFT) (SEQ ID NO:6); FA1090—Laz, orf NGO994, YP_208090.1 (SEQ ID NO:8); 1291—Laz, P07211.1, mis-annotated in GenBank as H.8 (SEQ ID NO:9).

FIG. 12. Amino acid sequence of MC58 Laz (SEQ ID NO:5). Shading shows similarity of the N-terminus with H.8. Underlining shows the signal peptide.

FIG. 13. MC58 (serogroup B) alignment of Lip (SEQ ID NO:1) and Laz (SEQ ID NO:5) (including signal polypeptide (also known as leader polypeptide) sequences that are lacking from the mature Lip and Laz proteins) showing conservation of certain portions. MC58-Lip/H.8, orf NMB1523, NP_274531, annotated as hypothetical protein MC58-Laz, orf NMB1533 NP_274540.1, mis-annotated in GenBank as H.8.

FIG. 14. Diverting blocking IgG away from the bacterial surface using peptides derived from the Lip sequence restores killing by monoclonal antibody JAR 3 directed against factor H binding protein (fHbp), a vaccine candidate antigen. The ability of JAR 3 to kill *Neisseria meningitidis* strain H44/76 in an in vitro serum bactericidal assay where the bacteria were incubated with JAR 3 (0.25 μg/ml) and blocking serum in which complement activity was preserved (called NK3; final concentration 20% (v/v) in the reaction mixture) is shown by the black bar labeled '1'.

FIG. 15. Immune IgG from mice immunized with recombinant Laz is specific for Laz and does not recognize Lip. Bacterial lysates of wild-type strain H44/76 (expresses Lip and Laz), H44/76 ΔLip (expresses only Lip but not Laz) and H44/76 ΔLaz (expresses Lip but not Laz) were incubated with serum from mice immunized with Laz at a dilution of 1:500 and bound IgG was detected using anti-mouse IgG conjugated to alkaline phosphatase.

FIG. 16. Immune serum collected 2 weeks after the final immunization was tested for its ability to kill wild-type serogroup B strain H44/76 in a serum bactericidal assay using human complement (serum from which IgG and IgM was depleted by sequential passage over the product protein G Separation-Pharmacia-Agarose column sold under the trademark protein G SEPHAROSE and anti-human IgM agarose, respectively) as a complement source (FIG. 16). JAR 3 plus complement was used as a positive control. Mouse serum plus complement was used undiluted (labeled as 'neat'; the final concentration of neat serum in the reaction mixture was 6.7% (v/v)), or at dilutions of 1:2, 1:4, 1:8, 1:16 and 1:32.

DEFINITIONS

To facilitate understanding of the invention, some terms are defined below.

"H.8," "Lip," "H.8 polypeptide" and "Lip polypeptide" interchangeably refer to the polypeptide sequence of *Neisseria meningitidis* membrane lipoprotein H.8 of approximately 100 amino acids. H.8 is named after a mouse hybridoma antibody that recognizes a surface epitope that is common to pathogenic *Neisseria* species including *Neisseria gonorrhoeae* and *Neisseria meningitidis* but absent from other commensal *Neisseria* species (Cannon et al., 1984. Infect Immun 43:994-999). Although the size and amino acid sequence of Lip can differ between *Neisseria* species and strains (Trees et al., 2000. J. Clin. Microbiol. 38:2914-2916), it primarily contains 11-20 pentameric AAEAP amino acid repeats and a lipid-modified N-terminal cysteine residue and lacks any aromatic residues (Woods et al., 1989. Mol Microbiol 3:43-48). This latter property makes it virtually undetectable by most protein assay and staining methods and thus makes it an elusive potential contaminant of preparations purified from outer membranes derived from *Neisseria*. H.8 (Lip) polypeptide is exemplified by, but not limited to, sequences shown in FIGS. 11 & 13 (SEQ ID NOs:1-4), that contain a Lip signal polypeptide sequence and the mature Lip polypeptide sequence.

The "Lip signal polypeptide sequence" is an N-terminal sequence that is cleaved following expression in *Neisseria meningitidis* to release the mature Lip polypeptide. In the exemplary strain MC58, the Lip signal polypeptide sequence is the N-terminal sequence from amino acid 1 to 17 of Lip SEQ ID NO:1 that aligns with the N-terminal sequence from amino acid 1 to 17 of Laz SEQ ID NO:5. The 17-amino acid signal sequence of MC58 Laz is underlined in FIG. 12. Lip signal polypeptide sequences from *Neisseria meningitidis* strains other than the MC58 strain (e.g., strains FAM18, Z2491, and FA1090 of FIG. 11) are those sequences that align with the N-terminal 17-amino acid MC58 Lip signal polypeptide sequence and/or align with the N-terminal 17-amino acid MC58 Laz signal polypeptide sequence (FIG. 11).

The mature Lip polypeptide sequence contains AAEAP (SEQ ID NO:10) repeats, and is exemplified by the strain MC58 sequence from amino acid 18 to 98 of SEQ ID NO:1 of FIG. 13. Mature Lip polypeptide sequences from *Neisseria meningitidis* strains other than the MC58 strain (e.g., strains FAM18, Z2491, and FA1090 of FIG. 11) are those sequences that align with the strain MC58 sequence from amino acid 8 to 98 of SEQ ID NO:1 of FIG. 13.

"Laz" and "Laz polypeptide" interchangeably refer to the polypeptide sequence of a lipid-modified azurin-like protein from *Neisseria*. H.8-specific monoclonal antibody is weakly cross-reactive to Laz, which contains imperfect AAEAP motifs at the N-terminal domain (approximately 50 amino acid portion) of the mature protein and a second domain with homology to the azurin protein of *Pseudomonas aeruginosa* (Gotschlich et al., 1987. FEMS Microbiol Lett 43:253-255; Kawula et al., 1987. Mol Microbiol 1:179-185; Woods et al., 1989. Mol Microbiol 3:583-591). Laz polypeptide is exemplified by, but not limited to, sequences shown in FIGS. 11-13 (SEQ ID NOs:5-9), that contain a Laz signal polypeptide sequence, and a mature Laz polypeptide sequence.

The "Laz signal polypeptide sequence" is an N-terminal sequence that is cleaved following expression in *Neisseria meningitidis* to release the mature Laz polypeptide. In the exemplary strain MC58, the Laz signal polypeptide sequence is the N-terminal sequence from amino acid 1 to 17 of Laz SEQ ID NO:5 (shown underlined in FIG. 12). Laz signal polypeptide sequences from *Neisseria meningitidis* strains other than the MC58 strain (e.g., strains FAM18, Z2491, FA1090 and 1291 of FIG. 11) are those sequences that align with the N-terminal 17-amino acid MC58 Laz signal polypeptide sequence. The mature Laz polypeptide sequence contains two regions, the "lip-like" region and the azurin domain.

The "Lip-like" region of the mature Laz polypeptide contains "imperfect" AAEAP repeats (i.e., pentameric peptides that do not have 100% identity to AAEAP), and is exemplified by the strain MC58 sequence from amino acid 18 to 61 of SEQ ID NO:5 of FIG. 13. Lip-like regions of Laz from *Neisseria meningitidis* strains other than the MC58 strain (e.g., strains FAM18, Z2491, FA1090 and 1291 of FIG. 11) are those sequences that align with the strain MC58 sequence from amino acid 18 to 61 of SEQ ID NO:5 of FIG. 13.

The "azurin domain" of the mature Laz polypeptide is exemplified by the strain MC58 sequence from amino acid 62 to 183 of SEQ ID NO:5 of FIG. 13. Laz azurin domains from *Neisseria meningitidis* strains other than the MC58 strain (e.g., strains FAM18, Z2491, FA1090 and 1291 of FIG. 11) are those sequences that align with the strain MC58 sequence from amino acid 62 to 183 of SEQ ID NO:5 of FIG. 13.

The term "portion" when used in reference to a protein (as in a "portion of a given protein") refers to a fragment of that protein that contains the entire amino acid sequence minus one or more amino acid residues. Thus, a portion of a protein may range in size from an exemplary 4, 10, 20, 30, and/or 50 contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

A "variant" or "homolog" of a polypeptide sequence of interest or nucleotide sequence of interest refers to a sequence that has at least 95% identity, at least 90% identity, at least 85% identity, at least 80% identity, at least 75% identity, at least 70% identity, and/or at least 65% identity with the an amino acid sequence of interest or nucleotide sequence of interest. Variants of a polypeptide sequence of interest may contain a mutation.

"Antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" includes polyclonal antibodies, monoclonal antibodies, naturally occurring antibodies as well as non-naturally occurring antibodies, including, for example, single chain, chimeric, bifunctional, de-immunized, and humanized antibodies, as well as antigen-binding fragments thereof, including, for example, Fab, $F(ab')_2$, Fab fragments, Fd fragments, Fc fragments, and Ev fragments of an antibody.

"Bactericidal antibody" refers to an antibody that, when binding to a bacterial antigen in a population of bacterial cells, results in killing (such as by bacteriolysis) from 10% to 100%, from 20% to 100%, from 30% to 100%, from 40% to 100%, from 50% to 100%, from 60% to 100%, from 70% to 100%, from 80% to 100%, and/or from 90% to 100% of the bacterial cells in the cell population. "Bactericidal activity" of a bactericidal antibody may be determined using methods disclosed herein (Examples 1-4) and known in the art, such as Goldschneider et al. (1969) J. Exp. Med. 129:1307-26; Borrow et al. (2005) Vaccine 23:2222-2227; Frasch et al. (2009) Vaccine 275:B112-B116; World Health Organization. Requirements for meningococcal polysaccharide vaccine. World Health Organization technical report series, no. 594. Geneva, Switzerland: World Health Organization; 1976. In particular embodiments, the assay of bactericidal activity employs complement from any source, such as human complement, baby rabbit complement, etc. In one embodiment, the bactericidal antibody is present in serum that is derived from a subject. *Neisseria meningitidis* bactericidal antibodies are known in the art and may be used as positive controls in *Neisseria meningitidis* bactericidal antibody assays, as well as to determine the presence of *Neisseria meningitidis* blocking antibody activity (further described below?). Commercially available *Neisseria meningitidis* bactericidal monoclonal antibodies include, without limitation, those obtained from the National Institute for Biological Standards and Control (NIBSC), Potters Bar Hertfordshire, U.K., such as antibodies specific for PorA molecules P1.7 (mAb MN14C11.6; NIBSC Order No. 01/514), P1.2 (mAb MN16C13F4; NIBSC Order No. 02/178) and P1.4 (mAb MN20B9.34; NIBSC Order No. 02/148). The bactericidal activity of these mAbs is previously described (Welsch et al. J Infect Dis. 2008 Apr. 1; 197(7):1053-61).

"Conserved" when referring to an amino acid, nucleotide, amino acid sequence, and/or nucleotide sequence in two molecules refers to 100% identity of the amino acid, nucleotide, amino acid sequence, and/or nucleotide sequence in the two molecules. Conserved sequences may be determined by sequence alignment (e.g., the shaded amino acids and sequences in FIGS. 11-13)

The terms "antigen," "immunogen," "antigenic," "immunogenic," "antigenically active," "immunologic," and "immunologically active" when made in reference to a molecule (e.g., H.8 and portions thereof, Laz and portions thereof), refer to any substance that is capable of inducing a specific humoral immune response (including eliciting a soluble antibody response) and/or cell-mediated immune response (including eliciting a cytotoxic T-lymphocyte (CTL) response).

In one embodiment, the antigen comprises an epitope. The terms "epitope" and "antigenic determinant" refer to a structure on an antigen that makes contact with a particular antibody variable region an/or T cell receptor as a result of molecular complementarity. When a protein or fragment of a protein is used to immunize a host animal, numerous regions of the protein may induce the production of antibodies which bind specifically to a given region or three-dimensional structure on the protein; these regions or structures are referred to as antigenic determinants. An epitope may compete with the intact antigen, from which it is derived, for binding to an antibody. Generally, secreted antibodies and their corresponding membrane-bound forms are capable of recognizing a wide variety of substances as antigens, whereas T cell receptors are capable of recognizing only fragments of proteins which are complexed with MHC molecules on cell surfaces.

The term "specifically binds" and "specific binding" when made in reference to the binding of two molecules (e.g. antibody to an antigen), etc., refers to an interaction of the two molecules that is dependent upon the presence of a particular structure on one or both of the molecules. For example, if an antibody is specific for epitope "A" on the molecule, then the presence of a protein containing epitope A (or free, unlabelled A) in a reaction containing labeled "A" and the antibody will reduce the amount of labeled A bound to the antibody. A particular molecule may exhibit specific binding to more that one other molecule.

"Mammal" refers to a rodent, primate (including simian and human) ovine, bovine, ruminant, lagomorph, porcine, caprine, equine, canine, feline, ave, etc. Preferred non-human animals are selected from the order Rodentia, such as mouse and rat, and may be used as models for testing the invention's compositions, kits, and methods.

As used herein, the term "at risk" for disease (such as infection with *Neisseria meningitidis*, refers to a subject (e.g., a human) that is predisposed to contracting and/or expressing one or more symptoms of the disease. Such subjects include those at risk for failing to elicit an immunogenic response to a vaccine against the disease (e.g., against infection with *Neisseria meningitidis*). This predisposition may be genetic (e.g., a particular genetic tendency to expressing one or more symptoms of the disease, such as heritable disorders, the presence of *Neisseria meningitidis* blocking antibodies, the presence of reduced levels of *Neisseria meningitidis* bactericidal antibodies, etc.), or due to other factors (e.g., environmental conditions, exposures to detrimental compounds, including immunogens, present in the environment, etc.). The term subject "at risk" includes subjects "suffering from disease," i.e., a subject that is experiencing the disease. It is not intended that the present invention be limited to any particular signs or symptoms. Thus, it is intended that the present invention encompass subjects that are experiencing any range of disease, from sub-clinical infection to full-blown disease, wherein the subject exhibits at least one of the indicia (e.g., signs and symptoms) associated with the disease.

The terms "reduce," "inhibit," "diminish," "suppress," "decrease," and grammatical equivalents (including "lower," "smaller," etc.) when in reference to the level of any molecule (e.g., amino acid sequence such as H.8, Laz, anti-H.8 antibody, anti-Laz antibody, etc., and nucleic acid sequence such as those encoding any of the polypeptides described herein), cell, and/or phenomenon (e.g., binding to a molecule, affinity of binding, expression of a nucleic acid sequence, transcription of a nucleic acid sequence, enzyme activity, bactericidal antibody activity, blocking antibody activity, etc.) in a first sample relative to a second sample, mean that the quantity of molecule, cell and/or phenomenon in the first sample is lower than in the second sample by any amount that is statistically significant using any art-accepted statistical method of analysis. In one embodiment, the quantity of molecule, cell and/or phenomenon in the first sample is at least 10% lower than, at least 25% lower than, at least 50% lower than, at least 75% lower than, and/or at least 90% lower than the quantity of the same molecule, cell and/or phenomenon in a second sample. In another embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in a second sample.

The terms "increase," "elevate," "raise," and grammatical equivalents (including "higher," "greater," etc.) when in reference to the level of any molecule (e.g., amino acid sequence such as H.8, Laz, anti-H.8 antibody, anti-Laz antibody, etc., and nucleic acid sequence such as those encoding any of the polypeptides described herein), cell, and/or phenomenon (e.g., binding to a molecule, affinity of binding, expression of a nucleic acid sequence, transcription of a nucleic acid sequence, enzyme activity, bactericidal antibody activity, blocking antibody activity, etc.) in a first sample relative to a second sample, mean that the quantity of the molecule, cell and/or phenomenon in the first sample is higher than in the second sample by any amount that is statistically significant using any art-accepted statistical method of analysis. In one embodiment, the quantity of the molecule, cell and/or phenomenon in the first sample is at least 10% greater than, at least 25% greater than, at least 50% greater than, at least 75% greater than, and/or at least 90% greater than the quantity of the same molecule, cell and/or phenomenon in a second sample. This includes, without limitation, a quantity of molecule, cell, and/or phenomenon in the first sample that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in a second sample.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

The term "change" refers to a qualitative and/or quantitative increase or decrease.

The term "antimicrobial" and "antimicrobial activity" when in reference to a compound (e.g., vaccine) refers to a compound that reduces the number of and/or rate of growth of a microbe compared to the number and/or rate of growth of the microbe in the absence of the compound. In one embodiment, the number of and/or rate of growth of a microbe in the presence of an antimicrobial compound is at least 10% lower than, at least 25% lower than, at least 50% lower than, at least 75% lower than, at least 90% lower than, at least 99%, and/or 100% lower than the number of and/or rate of growth of the microbe in the absence of the antimicrobial compound. In another embodiment, a 9-log number of microbe is reduced by at least 3-log, at least 5-log, at least 7-log, and/or at least 9-log in the presence of the antimicrobial compound.

An "antimicrobially effective amount" of a compound or composition (e.g., vaccine) refers to an amount of the compound or composition that has antimicrobial activity, including microbistatic amounts and microbicidal amounts.

An antimicrobial can be antibacterial, antifungal, antiviral and/or antinematode. An antimicrobial can be microbistatic, microbicidal, or both. An antimicrobial is "microbistatic" (e.g., bacteriostatic, fungistatic, etc.) if it reduces cell division by an amount less than 100%, without or without reducing cell viability. An antimicrobial is "microbicidal" (e.g., bactericidal, fungicidal, etc.) if it reduces cell viability by 100%, i.e., causes 100% cell death. Cell death is commonly detected by the absence of cell growth in liquid growth medium (e.g., absence of turbidity) or on a solid surface (e.g., absence of colony formation on agar). A "sterilizer," "sanitizer" and "disinfectant" are microbicidal. In contrast, a "preservative" is microbistatic. Certain microbistatic compositions are not bactericidal at any concentration.

Those of skill in the art know that composition that is microbistatic at a given concentration may be microbicidal at a higher concentration. Methods for determining antimicrobial activity are known in the art and disclosed herein (Example 2).

"Biological sample" refers to a composition that is obtained and/or derived from a biological source (e.g., animal), including body fluids (such as urine, blood, plasma, fecal matter, cerebrospinal fluid (CSF), semen, sputum, and saliva) as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like.

As used herein the terms "immunogenically-effective amount," "immunologically-effective amount" and "antigenically-effective amount" refer to that amount of a molecule that elicits and/or increases production of an immune response (including production of specific antibodies and/or induction of a TCL response) in a host upon vaccination. It is preferred, though not required, that the immunologically-effective (i.e., immunogenically-effective) amount is a "protective" amount. The terms "protective" and "therapeutic" amount of a composition refer to an amount of the composition that delays, reduces, palliates, ameliorates, stabilizes, and/or reverses one or more symptoms of a disease.

"One repeat" when in reference to a sequence refers to the presence of two copies of the sequence. The copies may be contiguous or non-contiguous.

"Outer membrane vesicle" and "OMV" contain an intact outer membrane, outer membrane proteins (OMP) and lipooligosaccharides (LOS) in their natural conformation and membrane environment. *Neisseria meningitidis* OMV vaccines have been administered intranasally and parenterally (Fisseha et al. (2005) Infection and Immunity 73:4070-4080).

The terms "purified," "isolated," and grammatical equivalents thereof as used herein, refer to the reduction in the amount of at least one undesirable component (such as cell type, protein, and/or nucleic acid sequence) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable cell type, protein and/or nucleic acid sequence in the sample.

DESCRIPTION OF THE INVENTION

One of the problems faced by the prior art is the wide variation among individuals within a population in their ability to kill meningococci in complement-dependent bactericidal assays. One reason for an inability to kill bacteria could be the lack of bactericidal antibody (Ab). A second reason for lack of serum bactericidal activity is the presence of antibody that interferes with the ability of otherwise bactericidal antibody to kill bacteria. These interfering antibodies are called "blocking antibodies."

"Blocking antibody" refers to an antibody that reduces the bactericidal activity of a bactericidal antibody. For example, a *Neisseria meningitidis* blocking antibody is an antibody that reduces the bactericidal activity of a *Neisseria meningitidis* bactericidal antibody. Blocking antibody activity may be determined using methods disclosed herein (Examples 1-4) and in the prior art. For example, with respect to *Neisseria meningitidis* infections, the prior art reported that convalescent sera from some patients recovering from meningococcal infection were less effective at killing meningococci than sera collected during the acute phase of infection. These sera could also block killing by otherwise bactericidal normal human sera (Thomas et al. 1943. J Clin Invest 22:375-385; Thomas et al. 1943. Immunological aspects. J Clin Invest 22:361-373). IgA purified from human serum on days 12, 33 and 27 following infection with groups B, C and Y meningococci, respectively, blocked complement-mediated bacteriolysis by the same sera. Blocking depended on the ratio of lytic to blocking antibody, was strain specific and was greater for IgG than for IgM (Griffiss, J. M. 1975. J Immunol 114:1779-84). In a separate study of 28 military recruits with meningococcal disease, 24 lacked bactericidal activity; removal of IgA from these 24 sera uniformly enhanced the bactericidal activity of IgM present in the same sera (Griffiss et al. 1977. J Infect Dis 136:733-9.). IgA1 directed against *Neisseria* meningitidis serogroup C polysaccharide blocked the bactericidal activity of IgG; blocking was not because of competitive inhibition of IgG binding and did not require the Fc region of IgA1 for blocking activity (Jarvis et al. 1991. J Immunol 147:1962-7).

Blocking antibody plays an important role in the pathogenesis of *Neisseria gonorrhoeae*. In a longitudinal study of 243 female commercial sex workers who experienced frequent gonococcal infection the presence of antibody to reduction modifiable protein (Rmp; protein III) were at increased risk of infection (adjusted odds ratio 3.4) (Plummer et al. 1993. J Clin Invest 91:339-43). Immunopurification studies confirmed the specificity of the gonococcal target for blocking antibodies as Rmp (Rice et al. 1986. J Exp Med 164:1735-1748). Antibody against Rmp can prevent killing by otherwise bactericidal antibody (Rice P A et al, 1986. J Exp Med. 164:1735-48). The presence of blocking anti-Rmp antibodies did not decrease C3 or C9 deposition on bacteria, suggesting that C3 could be diverted to alternative sites on the bacteria with formation of non-bactericidal C5b-9 (Joiner et al. J Clin Invest 76:1765-72). Rmp is not the only gonococcal target for blocking antibodies; IgA directed against the LOS of *Neisseria gonorrhoeae* could also block killing by otherwise bactericidal IgG (Apicella et al. 1986. J Infect Dis 153:520-526). In some instances, blocking antibodies may function by sterically hindering binding of bactericidal antibodies.

The protein homologous to Rmp in meningococci is called Class 4 protein. An anti-Class 4 monoclonal antibody (mAb) is able to block killing of *Neisseria meningitidis* by a mAb directed against Class 1 protein (Munkley A et al, 1991. Microb Pathog, 11:447-52). However, a subsequent study using serum from human volunteers vaccinated with an outer membrane vesicle vaccine that contained the Class 4 protein as one of its constituents did not exert any significant blocking effects, even though anti-Class 4 Abs) were elicited (Rosenqvist et al, Infect Immun, 1999; 67(3): 1267-76).

Prior art studies of blocking antibody in *Neisseria* have largely focused on the Rmp or Class 4 proteins. The ability of antibody directed against other membrane antigens has not been investigated.

The classical complement pathway is essential for bactericidal (and opsonic) antibody (Ab) mediated vaccine induced immunity against *Neisseria meningitidis*. Colonization is an immunizing process and natural antibody may play a key role in protection against invasive disease. There is a large variation in complement-dependent bactericidal activity among sera from non-immunized individuals. In some instances, despite high levels of antibody binding, killing does not occur. Antibody directed against certain bacterial targets may not activate complement, and in some instances, may even block killing by otherwise bactericidal antibody.

The invention is premised, at least in part, on the inventors' discovery that the ability of the bacteria to elicit such blocking antibody may provide an important means to evade the host. As an example, reduction modifiable protein (Rmp) of *N. gonorrhoeae* has been shown to be a target of blocking antibodies. Data herein shows the presence of blocking antibodies against serogroup B *Neisseria meningitidis* in the serum of certain healthy individuals. Data herein also evaluated the Rmp homologue in *Neisseria meningitidis* as a potential target for blocking antibodies.

The invention also provides the inventors' discovery that *Neisseria meningitidis* membrane lipoprotein H.8 is and antigen that is a target for blocking Ab. This discovery is important because the presence of blocking antibody may; i) predispose individuals to developing invasive disease with *Neisseria meningitidis*, ii) decrease the efficacy of meningococcal vaccines (such as the currently used polysaccharide based vaccines or protein vaccines under development) in such individuals and iii) decrease the efficacy of meningococcal outer membrane vesicle (OMV) vaccines that may contain H.8 in persons who develop high titers of anti-H.8 antibody in response to vaccination.

Data herein, consistent with previous reports, shows that serum from different human subjects varies in its ability to kill meningococci in serum bactericidal assays. The inventors have also discovered that antibodies directed against the meningocoal H.8 function as blocking antibodies.

The inventors discovered that adding heat-inactivated serum (heating inactivates complement, but preserves activity of Ab) from individuals who lack bactericidal activity to intact serum from individuals who exhibit killing of meningococci, resulted in decreased bacterial killing by the latter. The inventors concluded that the heat inactivated serum from the non-killing sera contained blocking activity.

The inventors analyzed the specificity of antibody from killing and blocking sera and observed that blocking sera contained IgG directed against a *Neisseria meningitidis* membrane lipoprotein called H.8 (Strittmatter et al., J Exp Med. 1986; 164(6):2038-48; Woods et al, Mol. Microbiol. 1989; 3(1):43-8). About 15% (3 of 19) of the sera tested by the inventors possessed blocking activity. Anti-H.8 antibody was not present or was present in small amounts relative to bactericidal antibody in the killing sera that were analyzed. Depletion of IgG from the blocking sera resulted in loss of its blocking activity. Furthermore, loss of blocking activity occurred when an isogenic mutant meningococcal strain deficient in H.8 was used as the test organism.

The invention is further described under A) Screening Subjects, B) Kits, and C) Vaccines.

A) Screening Subjects

The invention provides methods for identifying a mammalian subject at risk for contracting meningococcal disease and/or at risk for failing to elicit an immunogenic response to a vaccine against *Neisseria meningitidis*, comprising a) providing a biological sample from the subject, and b) detecting in the biological sample an antibody that specifically binds to one or more of *Neisseria meningitidis* 1) H.8, 2) antigenic portion of H.8, 3) Laz, and 4) antigenic portion of Laz. In one embodiment, these methods are useful for identifying subjects with high titers of naturally occurring anti-H.8 antibody who potentially may be at a higher risk for contracting meningococcal disease, and in preventing vaccine failures in 10% to 20% of vaccine recipients by, for example, administering booster vaccine doses.

While the invention is illustrated using the antigenic H.8 which elicits blocking antibodies, it is expressly contemplated that the invention also encompasses antigenic portions of one or both of H.8 and Laz. Exemplary antigenic portions of H.8 and Laz are those that contain one or more amino acid(s) that are conserved in *Neisseria meningitidis* H.8 and *Neisseria meningitidis* Laz, such as those shaded amino acids shown in FIGS. 11-13.

Figure 11:
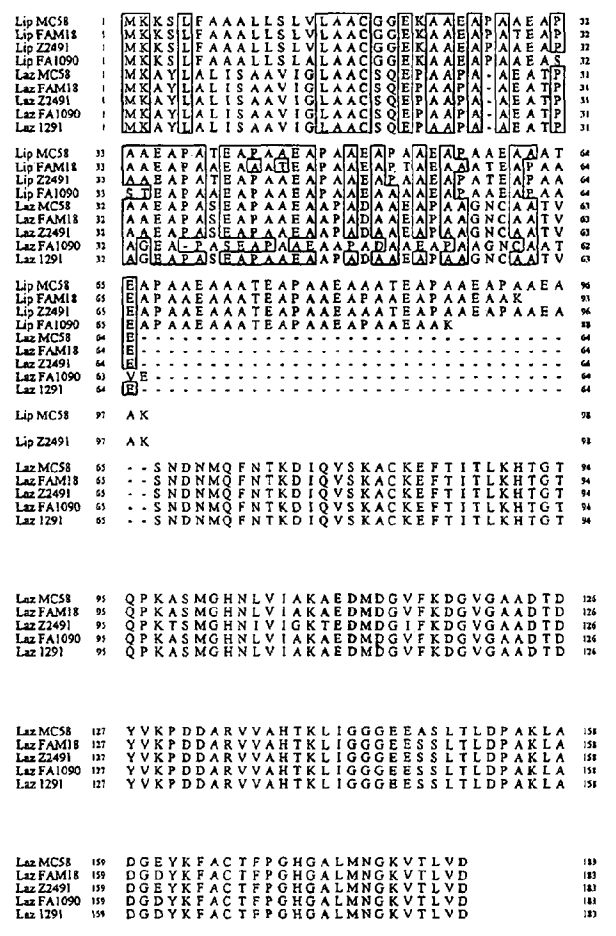

In another embodiment, the antigenic portion of one or both of H.8 and Laz contains a pentameric sequence AAEAP, such as those shaded amino acids shown in FIGS. 11-13.

In one embodiment, detecting subjects at risk includes detecting a level of the antibody that specifically binds to H.8 in the subject that is higher than the level of the antibody in a control subject that has not been infected with *Neisseria meningitidis* and has not been vaccinated against *Neisseria meningitidis*. In another embodiment, detecting involves observing a level of the antibody that specifically binds to Laz in the subject that is higher than the level of the antibody in a control subject that has not been infected with *Neisseria meningitidis* and has not been vaccinated against *Neisseria meningitidis*. In yet another embodiment, the method involves detecting a level of the antibody that specifically binds to the antigenic portion of H.8 in the subject that is higher than the level of the antibody in a control subject that has not been infected with *Neisseria meningitidis* and has not been vaccinated against *Neisseria meningitidis*. In a further embodiment, the level of the antibody that specifically binds to the antigenic portion of Laz in the subject is higher than the level of the antibody in a control subject that has not been infected with *Neisseria meningitidis* and has not been vaccinated against *Neisseria meningitidis*.

The invention is not limited to the type of method used for detecting antibodies in the biological samples from subjects.

Thus in some embodiments, antibody detection utilizes known assays such as radioimmunoassays, "sandwich" immunoassays such as ELISA (enzyme-linked immunosorbant assay), and ELISpot (enzyme-linked immunosorbent spot assay), immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc. For example, to determine whether an antibody binds to H.8, any known binding assay may be employed. For example, H.8 may be immobilized on a surface and then contacted with labeled H.8 antibody (e.g., using the BIAcore system) to measure the amount of H.8 antibody that bind. Using an indirect system, the quantity of H.8 antibody can be measured in the same system by using a labeled anti-human IgG. A standard curve can be established to determine known concentrations of H.8 antibody that binds to H.8. This can be used to compare amounts of H.8 antibody in unknown specimens. Screening for H.8 antibody can also be accomplished by determining the antibody concentration that binds to a fixed target (as above) comprised of whole *Neisseria meningitidis* organisms and separately to a genetic mutant of whole *Neisseria meningitidis* that lacks H.8 (ΔH.8-*Neisseria meningitidis*). The difference between the two measurements will represent the amount of H.8 antibody present.

Screening for antibodies can also be carried out utilizing a competition assay. For example, if the H.8 antibody binding agent being tested competes with an anti-H.8 monoclonal antibody for binding to H.8 antigen, as shown by a decrease in binding of the monoclonal antibody, then it is likely that the agent and the anti-H.8 monoclonal antibody bind to the same, or a closely related, epitope. Using known concentrations of H.8 antibody as standards the amount of H.8 antibody can be measured.

One of the advantages of the invention is that persons identified using the invention's methods as having relatively high titers of naturally occurring antibody that is specific for H.8, antigenic portions of H.8, Laz, and/or antigenic portions of Laz, may also be identified as having a higher risk for contracting meningococcal disease. Thus, these subjects may benefit from receiving a meningococcal vaccine.

Because these subjects may also have lower killing (bactericidal) titers following administration of meningococcal vaccines, it may therefore be useful to test the sera of such persons for bactericidal activity following vaccination. These individuals may also benefit from booster doses of the vaccine to elicit adequate protective bactericidal antibody responses. Methods for determining bactericidal activity are known in the art and described herein (Example 2).

Thus, the invention's methods for detecting antibodies that are specific for H.8, Laz, and/or portions of H.8 and/or Laz, are useful in subjects that are not infected with *Neisseria meningitidis* and/or vaccinated with a vaccine against *Neisseria meningitidis*. In another embodiment, the subject may be one that has already been infected with *Neisseria meningitidis* and/or vaccinated against *Neisseria meningitidis*. In that instance, the methods may be used to determine whether the antibodies are bactericidal, and have immunogenic activity against *Neisseria meningitidis*.

While data herein used serum from subjects to test the levels of antibodies, the invention is not limited to the type or source of the biological sample, so long as the sample may be processed for detection of antibody. Preferred biological samples include, but are not limited to serum, blood, saliva, and urine.

B) Kits

The invention provides kits for detecting the presence of an antibody that specifically binds to a *Neisseria meningitidis* polypeptide. In one embodiment, the polypeptide is one or more of a) H.8, b) antigenic portion of H.8, c) Laz, and d) antigenic portion of Laz. The term "kit" is used in reference to a combination of reagents and other materials. It is contemplated that the kit may include reagents such as buffering agents, nucleic acid stabilizing reagents, protein stabilizing reagents, signal producing systems (e.g., fluorescence generating systems such as fluorescence resonance energy transfer (FRET) systems, radioactive isotopes, etc.), antibodies, substrate proteins (e.g., H.8, antigenic portion of H.8, Laz, antigenic portion of Laz, etc.), control proteins, control nucleic acid sequences, as well as testing containers (e.g., microtiter plates, etc.). It is not intended that the term "kit" be limited to a particular combination of reagents and/or other materials. In one embodiment, the kit further comprises instructions for using the reagents. The test kit may be packaged in any suitable manner, typically with the elements in a single container or various containers as necessary along with a sheet of instructions for carrying out the test. In some embodiments, the kits also preferably include a positive control sample. Kits may be produced in a variety of ways that are standard in the art. In some embodiments, the kits contain at least one reagent for detecting and/or quantifying the level of an antibody. In preferred embodiments, the instructions specify that risk for developing a disease or condition is determined by detecting the presence and/or elevated levels of an antibody in the subject. In one embodiment, the kit comprises a solid support (e.g., microtiter plate) to which one or more of the invention's polypeptides and/or antibodies are immobilized.

C) Vaccines

The invention additionally provides vaccines against *Neisseria meningitidis* comprising *Neisseria meningitidis* polypeptides that contain at least one mutation in at least one of *Neisseria meningitidis* a) H.8, b) antigenic portion of H.8, c) Laz, and d) antigenic portion of Laz, wherein the mutation renders the mutated *Neisseria meningitidis* polypeptide non-antigenic. These vaccines are premised on the inventors' above discussed discovery, and their view that breakthrough cases of disease after administration of meningococcal disease vaccines, such as MenZB and MenBvac vaccines, were the result of the presence of H.8 (and/or Laz) in these outer membrane vesicle vaccines, and that the resulting anti-H.8 blocking antibody and/or anti-Laz blocking antibody in the immunized subjects may have reduced the efficacy of the vaccine. A vaccine that lacks H.8, Laz, and/or antigenic portions thereof is likely be more effective because blocking antibody against meningicocci will not be elicited.

The term "vaccine" refers to a preparation that may be administered to a host to induce a humoral immune response (including eliciting a soluble antibody response) and/or cell-mediated immune response (including eliciting a CTL response). Vaccines may contain pharmaceutically acceptable carriers, diluents or excipients. Vaccines include "live attenuated vaccine," which refers to a pathogenic organism that has reduced pathogenicity compared the live wild-type organism, and that still induces specific immunity against the pathogenic organism. In one embodiment, an attenuated bacteria is capable of multiplying in the host, and provides continuous antigenic stimulation over a period of time.

Vaccines include marker vaccines and non-marker vaccines. A "marker vaccine" is a vaccine that allows serological differentiation between vaccinated and wild-type virus infected animals. In one embodiment, the differentiation of vaccinated and infected animals is based on detecting the presence of a mutation (e.g., deletion) of one or more nucleotide sequence and/or protein sequence in the vaccine compared to the wild type micro-organism. A "non-marker vaccine" is a vaccine that does not allow serological differentiation between vaccinated and wild-type virus infected animals.

A "serological marker" is a molecule (e.g., amino acid sequence, nucleotide sequence) that is used to distinguish a specific disease or organism in a subject. Serological markers are useful for identifying the presence of the organism and early stages of the disease, prior to the onset of symptoms.

Vaccines may contain an adjuvant. The term "adjuvant" as used herein refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), Titer Max adjuvant (CytRx), Cystine phosphate Guanine (CpG) and Quil A adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

Vaccines may be formulated using a diluent. Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

Vaccines may contain an excipient. The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

The invention is not limited to the type of mutation that is introduced into *Neisseria meningitidis* nucleotide and/or polypeptide sequences (such as mutations that render the *Neisseria meningitidis* polypeptide non-antigenic). Thus, the mutation may be a deletion, insertion, and/or substitution.

The terms "mutation" and "modification" refer to a deletion, insertion, and/or substitution. Thus, a "mutant polypeptide" is a polypeptide that contains one or more deletion, insertion, and/or substitution. A "deletion" is defined as a change in a nucleic acid sequence or amino acid sequence in which one or more nucleotides or amino acids, respectively, is absent. An "insertion" or "addition" is that change in a nucleic acid sequence or amino acid sequence that has resulted in the addition of one or more nucleotides or amino acids, respectively. An insertion also refers to the addition of any synthetic chemical group. A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative.

A "conservative substitution" of an amino acid refers to the replacement of that amino acid with another amino acid that has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine my be conservatively substituted one for the other since each is a basic, charged (hydrophilic) amino acid.

"Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

The invention's methods are particularly useful in preparing "outer membrane vesicle" (OMV) vaccines, since these vaccines are likely to be contaminated with at least an antigenic portion of H.8 and/or Laz. Methods for preparing *Neisseria meningitidis* OMV vaccines are know in the art, as exemplified by, but not limited to, U.S. Pat. Nos. 4,601,903; 7,118,757; 6,627,204; 7,018,636; 7,025,963; 4,271,147; U.S. Pat. Application No. US 2004/0249125; and Wedege E et al. Clin Vaccine Immunol. 2007; 14(7):830-838.

The invention's methods are also useful in preparing *Neisseria meningitidis* polysaccharide vaccines, since these vaccines may be contaminated with trace amounts of H.8, Laz, and/or antigenic portions thereof that may elicit blocking antibodies. Methods for preparing *Neisseria meningitidis* polysaccharide vaccines are know in the art, as exemplified by, but not limited to those in European Pat. No. 1,534,342.

While the invention has been illustrated with serogroup B of *Neisseria meningitidis*, it is nonetheless expressly contemplated that the compositions and methods herein are equally efficacious with any *Neisseria meningitidis* serogroup (generally classified based on the chemical composition of the bacterial capsular polysaccharide) that expresses H.8 and/or Laz, including serotypes A, B, C, D, 29E, H, I, K, L, W-135, X, Y and Z. In addition, the invention is also applicable to emerging rare cases of invasive meningococcal disease that are cause by unencapsulated meningococci (capsule null isolates) (Findlow et al, J. Infect. Dis. 2007 Apr. 1; 195(7):1071-7; Hoang L M et al, Clin Infect Dis. 2005 Mar. 1; 40(5):e38-42).

Also provided by the invention are methods for producing a vaccine, comprising a) providing Neisseria meningitidis that comprises a mutation in one or more of Neisseria meningitidis 1) H.8, 2) antigenic portion of H.8, 2) Laz, and 2) antigenic portion of Laz, and b) using the mutant to prepare a vaccine comprising a Neisseria meningitidis protein. Vaccines that lack the antigenic H.8, Laz and/or portions thereof (such as those made from an H.8 deletion mutant) are likely to overcome potential obstacles of reduced vaccine efficacy due to eliciting blocking Ab. Mutant Neisseria meningitidis may be produced using standard methods, such as those in Example 1 that describes a H.8 null mutant. Exemplary wild type Neisseria meningitidis that may be used to obtain mutants lacking H.8 antigen, Laz antigen, and/or antigenic portions thereof includes strain H4476 (B:15:P1.7,16) deposited on Dec. 11, 1989 in the Centraal Bureau voor Schimmelculturen (CBS), Baarn, The Netherlands and has deposit number CBS 635.89.

The invention also provide methods for immunizing a mammalian subject, comprising a) providing 1) a vaccine as described herein, and 2) a mammalian subject, and b) administering an immunologically effective amount of the vaccine to the subject to produce an immune response. The immune response may elicit an antibody and/or T lymphocytes that specifically bind to one or more of i) H.8, ii) antigenic portion of H.8, iii) Laz, and vi) antigenic portion of Laz.

EXPERIMENTAL

The following examples serve to illustrate certain preferred embodiments and aspects of the present invention and are not to be construed as limiting the scope thereof.

EXAMPLE 1

Construction of the H.8 Knockout Mutant in Neisseria Meningitidis

Plasmid pHSS6ΔH.8 that contained the H.8 gene that was insertionally inactivated with the chloramphenicol resistance cassette was provided by Dr. Janne Cannon, University of North Carolina, Chapel Hill, N.C. (Woods et al., 1989 Mol Microbiol 3:43-48.). This plasmid was used to transform Neisseria gonorrhoeae strain F62 as described previously (Fisette et al., 2003. The lip lipoprotein from Neisseria gonorrhoeae stimulates cytokine release and NF-kB activation in epithelial cells in a TLR2-dependent manner. J Biol. Chem.). Chromosomal DNA was then prepared from the H.8 deletion mutant of Neisseria gonorrhoeae strain F62 and used to transform Neisseria meningitidis strains MC58 and H44/76 by homologous recombination. Chloramphenicol-resistant clones were selected and loss of H.8 was confirmed by western blotting with a mAb against H.8. The above method may be used with other Neisserial strains, since they are naturally competent and making bacterial mutants is routine in the art.

EXAMPLE 2

Variation in Bactericidal Activity Against Neisseria Meningitidis

This study was carried out to determine the possible reasons for variations in bactericidal activity among individuals against serogroup B Neisseria meningitidis.

Methods: Sera obtained from 19 healthy individuals were screened for bactericidal activity against serogroup B strain H44/76. Sera that decreased CFU >70% of bacteria were termed bactericidal, sera that killed <20%, non-bactericidal. Heat-inactivated non-bactericidal serum was added to bactericidal sera to screen for blocking activity. IgG purified from blocking sera were used to confirm that this class of antibody possessed blocking activity. In addition, we determined if blocking antibody was directed against the Neisseria meningitidis Class IV outer membrane lipoprotein H.8, which is a homologue of gonococcal Rmp. We used an isogenic Class IV protein H.8 deletion mutant of serogroup B H44/76 and compared the level of blocking directed against wild type H44/76 to its isogenic Class IV protein H.8 deletion mutant. The H.8 deletion mutants in meningococci were created using DNA derived from a gonococcal H.8 mutant obtained from Dr. Janne Cannon at the University of North Carolina.

One of the monoclonal antibodies used in this investigation is JAR 3. Factor H binding protein (fHbp), previously called GNA1870 (Novartis) or LP2086 (Wyeth), is currently the leading meningococcal protein vaccine candidate. Several monoclonal antibodies (mAbs) directed against fHbp are bactericidal—one such mAb is called JAR 3.

Results: The results are shown in FIGS. 1-10. Out of the 19 individual sera 4 were non bactericidal, 4 were bactericidal, while the remaining 11 sera showed intermediate killing. Also, 3 out of 4 of the non-bactericidal sera blocked killing of serogroup B H44/76 by 2 of the 4 bactericidal sera. One of the non-bactericidal sera failed to block killing of any of the bactericidal sera, while two of the bactericidal sera were not blocked by any of the non-bactericidal sera. Experiments using purified antibody confirmed that blocking was mediated by IgG. Furthermore, blocking serum depleted of IgG did not have any residual blocking activity, affirming IgG as the blocking factor. Blocking was also seen with a serogroup A strain, suggesting that blocking antibody was not directed against capsule. Deleting Class IV protein from Neisseria meningitidis did not abrogate blocking, strongly suggesting that distinct from N. gonorrhoeae, blocking antibody against Neisseria meningitidis was not directed against Class IV protein. Western blot experiments showed novel IgG targets recognized by blocking sera that were not otherwise identified by non-blocking sera.

Conclusions: Bactericidal assays done using 10% serum obtained from a randomly selected population of healthy individuals showed wide variation in the ability to kill serogroup B Neisseria meningitidis. In addition, 3 of 4 of the non-killing sera tested could block killing by otherwise bactericidal sera. The results also show that this blocking activity is mediated mainly by serum IgG. Both heat inactivated and purified IgG from blocking serum inhibited the bactericidal activity of killing serum. The data also show that the blocking antibody was directed against Neisseria outer membrane protein H.8/Lip. Blocking antibody can also block killing by specific antibody such as a mAb directed against the vaccine candidate fHbp (GNA1870 or LP2086). In sum, the results demonstrate the identification of novel targets (H.8) of blocking antibodies and their

EXAMPLE 3

Figure 14:
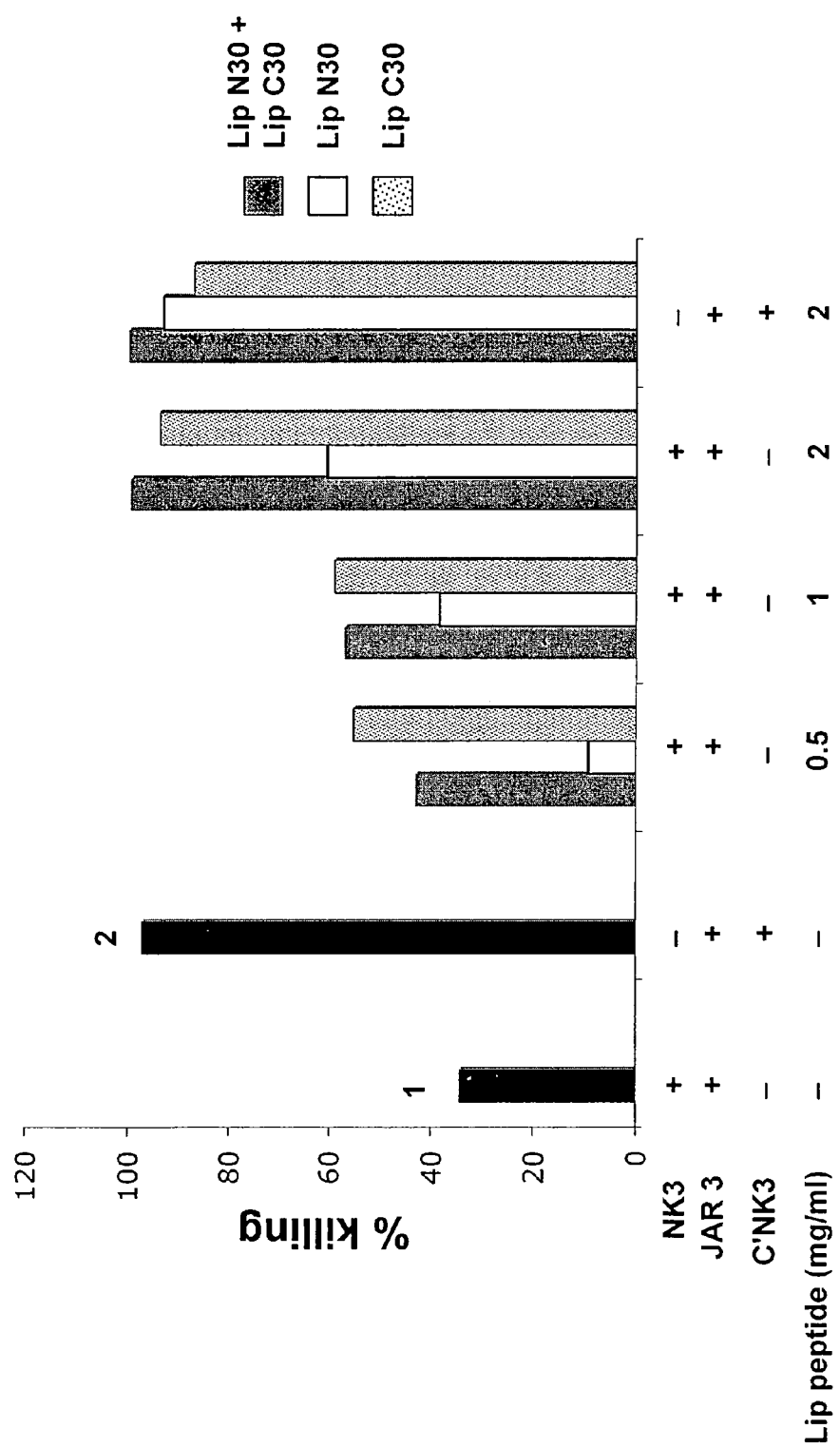

Each of Lip N30 and Lip C30 Polypeptides Restore *Neisseria Meningitidis* Killing by a Bactericidal Antibody To determine the specificity of the blocking antibody in NK3, peptides that correspond to the N-terminal 30 amino acids of the mature Lip protein (called Lip N30; sequence—CGGEKAAEAPAAEAPAAEAPATEAPAAEAP (SEQ ID NO:13) that represents amino acids 18-47 of the Lip sequence in FIG. 13) or against the 30 C-terminal amino acids of the mature Lip protein (called Lip C30; amino acids 69-98 plus an N-terminal added Cys residue (italicized and underlined)—_C_AEAAATEAPAAEAAATEAPAAEAPAAEAAK (SEQ ID NO:11)) were synthesized (Genway Biotech) and added to NK3 in the bactericidal assay. The peptides were used either alone (Lip N30 indicated by the white bars and Lip C30 by the patterned grey bars) or in combination (solid grey bars) and their final concentrations in the reaction mixture ranged from 0.5 to 2 mg/ml. As seen in FIG. 14, increasing the amounts of the peptide in the serum could progressively enhance complement-dependent killing by monoclonal antibody JAR 3 in the presence of NK3 (contains blocking antibody). As an additional control, the presence of the peptides in a reaction mixture containing monoclonal antibody JAR 3, complement (C'NK3; devoid of blocking Antibody) and bacteria did not affect complement-dependent killing by JAR 3 (similar killing seen when JAR 3 was added to C'NK3 (black bar marked '2')).

FIG. 14 shows depleting IgG and IgM from NK3 to yield complement derived from NK3 (C'NK3; final concentration in the reaction mixture was 20% (v/v)) restored killing of H44/76 by JAR 3 (black bar labeled '2').

On a molar basis, peptide Lip C30 was more effective in restoring killing than peptide Lip N30. These data provide additional specificity for the targets of blocking Antibody against *Neisseria meningitidis*.

EXAMPLE 4

Serum from Mice Immunized with Recombinant Laz is Specific for Laz and is Bactericidal Against *Neisseria Meningitidis* Strain H44/76

Recombinant Laz (spanning amino acids from 19 to 183 of Laz sequence of FIG. 13) that contained a C-terminal 6×His-tag was expressed in *E. coli* BL-21 and purified by $Ni^{2+}$-affinity chromatography. Six-week old Balb/c mice were immunized with 25 μg of recombinant Laz absorbed with aluminum hydroxide (Alum) as an adjuvant at week 0 followed by booster doses at weeks 3 and 6 using 50 μg of recombinant Laz absorbed with Alum.

Figure 15:
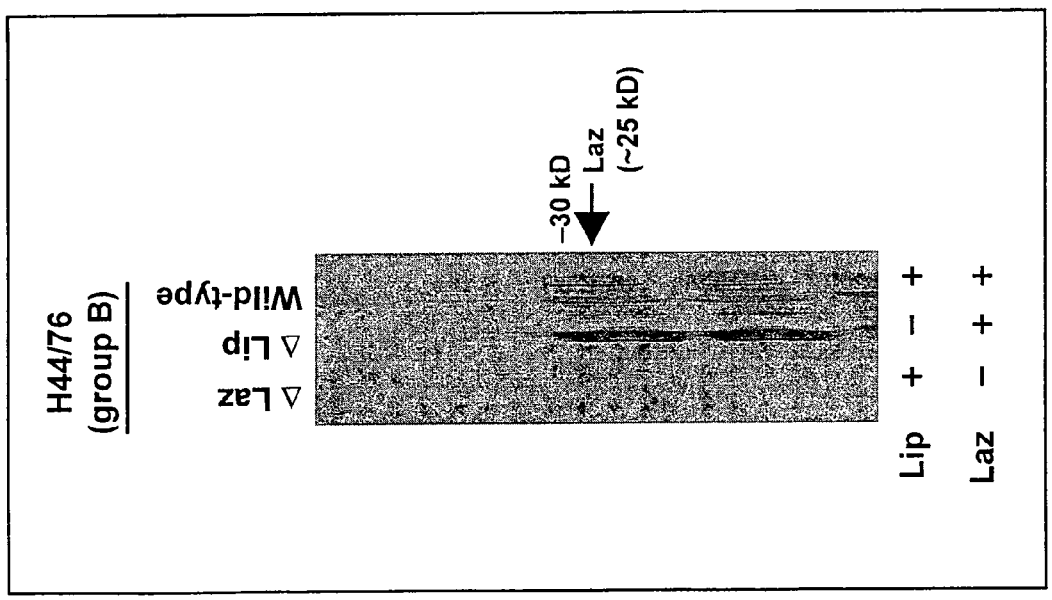

FIG. 15 shows that only Laz-expressing meningococci showed reactivity with immune serum, confirming that the elicited Antibody reacts with Laz but not the epitopes on Lip (such as the AAEAP pentapeptide repeats)

Figure 16:
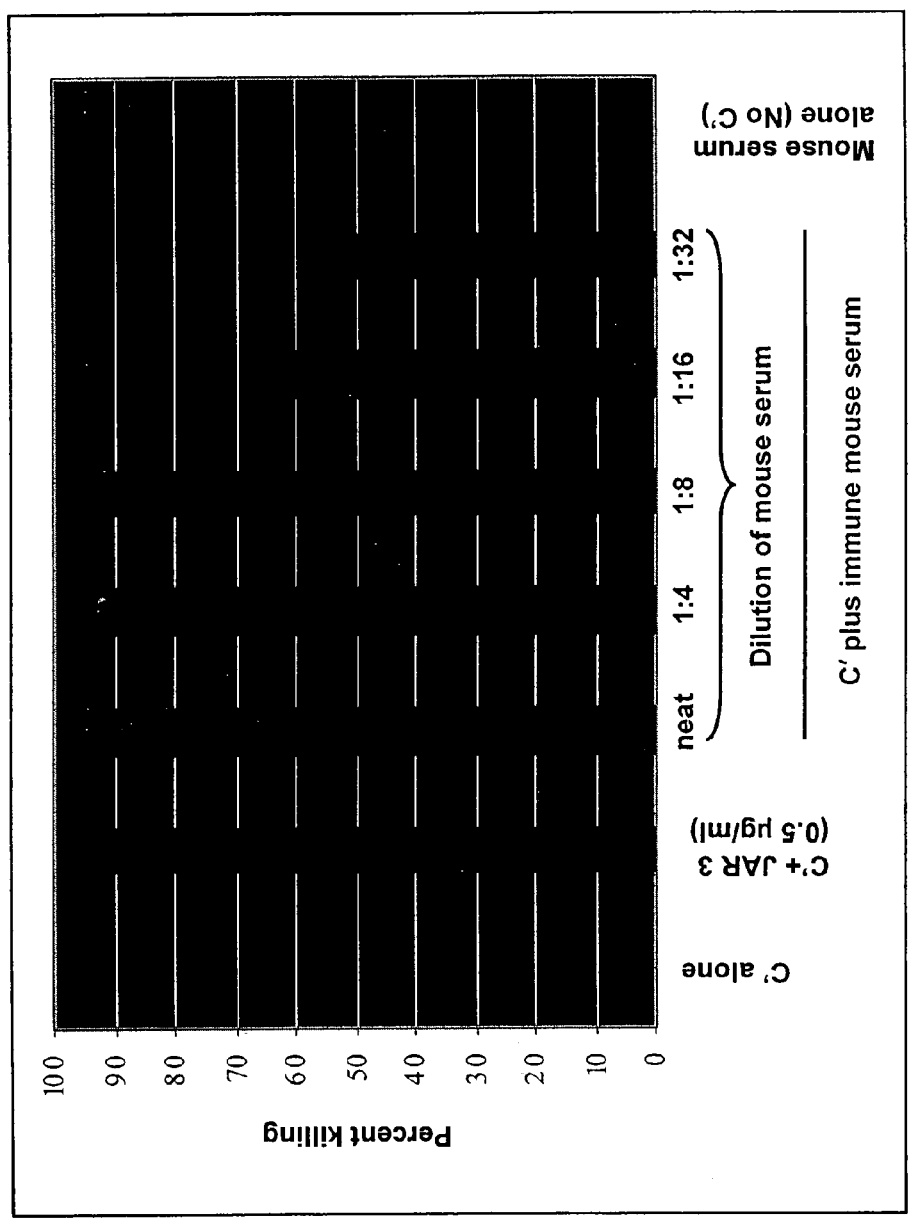

Immune serum collected 2 weeks after the final immunization was tested for its ability to kill wild-type serogroup B strain H44/76 in a serum bactericidal assay using human complement (serum from which IgG and IgM was depleted by sequential passage over the product protein G Separation-Pharmacia-Agarose column sold under the trademark protein G SEPHAROSE and anti-human IgM agarose, respectively) as a complement source (C') (FIG. 16). C' alone did not result in any killing. JAR 3 plus complement was used as a positive control and resulted in approximately 93% bacterial killing. Mouse serum plus complement resulted in comparable killing when used undiluted (labeled as 'neat'; the final concentration of neat serum in the reaction mixture was 6.7% (v/v)), or at dilutions of 1:2, 1:4 or 1:8; a dose-responsive decrease in killing was seen when the mouse serum was further diluted to 1:16 and 1:32. The mouse serum had no effect on bacterial survival in the absence of added complement (C').

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A mutant *Neisseria meningitidis* that lacks one or more polypeptide sequences that specifically bind to a *Neisseria meningitidis* blocking antibody, wherein said one or more polypeptide sequences are selected from the group consisting of
   a) H.8 polypeptide sequence selected from the group consisting of SEQ ID NO: 1, SEQ ID NO: 2, and SEQ ID NO: 3, and
   b) H.8 polypeptide sequence that lacks one or more H.8 portions selected from the group consisting of:
      1) from amino acids 18 to 98 of SEQ ID NO: 1,
      2) from amino acids 18 to 93 of SEQ ID NO: 2, and
      3) from amino acids 18 to 98 of SEQ ID NO: 3.

2. The mutant of claim 1, wherein said mutant
   i) lacks said H.8 polypeptide sequence selected from the group consisting of SEQ ID NO: 1, SEQ ID NO: 2, and SEQ ID NO: 3, and
   ii) comprises a deletion of Laz polypeptide that specifically binds to said *Neisseria meningitidis* blocking antibody, wherein said Laz polypeptide is selected from the group consisting of SEQ ID NO:5, SEQ ID NO: 6, and SEQ ID NO: 7.

3. The mutant of claim 1, wherein said mutant
   i) lacks said H.8 polypeptide sequence selected from the group consisting of SEQ ID NO: 1, SEQ ID NO: 2, and SEQ ID NO: 3, and ii) comprises a Laz polypeptide that lacks one or more Laz portions, wherein said one or more Laz portions specifically bind to said *Neisseria meningitidis* blocking antibody and are selected from the group consisting of
1) at least one repeat of AAEAP (SEQ ID NO: 10),
2) from amino acids 18 to 61 of SEQ ID NO: 5,
3) from amino acids 18 to 61 of SEQ ID NO: 6, and
4) from amino acids 18 to 61 of SEQ ID NO: 7.

4. The mutant of claim 1, wherein said mutant
i) comprises said H.8 polypeptide sequence that lacks the one or more H.8 portions, and
ii) comprises a deletion of Laz polypeptide that specifically binds to said *Neisseria meningitidis* blocking antibody, wherein said Laz polypeptide is selected from the group consisting of SEQ ID NO: 5, SEQ ID NO: 6, and SEQ ID NO: 7.

5. The mutant of claim 1, wherein said mutant
i) comprises said H.8 polypeptide sequence that lacks the one or more H.8 portions, and
ii) comprises a Laz polypeptide that lacks one or more Laz portions, wherein said one or more Laz portions specifically bind to said *Neisseria meningitidis* blocking antibody and are selected from the group consisting of
1) at least one repeat of AAEAP (SEQ ID NO: 10),
2) from amino acids 18 to 61 of SEQ ID NO: 5,
3) from amino acids 18 to 61 of SEQ ID NO: 6, and
4) from amino acids 18 to 61 of SEQ ID NO: 7.

6. The mutant of claim 1, wherein said mutant lacks said H.8 polypeptide sequence selected from the group consisting of SEQ ID NO: 1, SEQ ID NO: 2, and SEQ ID NO: 3.

7. A mutant *Neisseria meningitidis* that comprises a mutant H.8 polypeptide, wherein said mutant H.8 polypeptide lacks the H.8 portion from amino acids 18 to 98 of SEQ ID NO: 1.

8. A composition comprising an outer membrane vesicle (OMV) prepared from the mutant *Neisseria meningitidis* of claim 1.

* * * * *

SEQUENCE LISTING

```
<160> NUMBER OF SEQ ID NOS: 13

<210> SEQ ID NO 1
<211> LENGTH: 98
<212> TYPE: PRT
<213> ORGANISM: Neisseria meningitidis

<400> SEQUENCE: 1

Met Lys Lys Ser Leu Phe Ala Ala Ala Leu Leu Ser Leu Val Leu Ala
1               5                   10                  15

Ala Cys Gly Gly Glu Lys Ala Ala Glu Ala Pro Ala Ala Glu Ala Pro
            20                  25                  30

Ala Ala Glu Ala Pro Ala Thr Glu Ala Pro Ala Ala Glu Ala Pro Ala
        35                  40                  45
```

```
Ala Glu Ala Pro Ala Ala Glu Ala Pro Ala Glu Ala Ala Thr
    50                  55                  60

Glu Ala Pro Ala Ala Glu Ala Ala Thr Glu Ala Pro Ala Ala Glu
65                  70                  75                  80

Ala Ala Ala Thr Glu Ala Pro Ala Ala Glu Ala Pro Ala Ala Glu Ala
                85                  90                  95

Ala Lys

<210> SEQ ID NO 2
<211> LENGTH: 93
<212> TYPE: PRT
<213> ORGANISM: Neisseria meningitidis

<400> SEQUENCE: 2

Met Lys Lys Ser Leu Phe Ala Ala Ala Leu Leu Ser Leu Val Leu Ala
1               5                   10                  15

Ala Cys Gly Gly Glu Lys Ala Ala Glu Ala Pro Ala Thr Glu Ala Pro
                20                  25                  30

Ala Ala Glu Ala Pro Ala Ala Glu Ala Ala Thr Glu Ala Pro Ala
            35                  40                  45

Ala Glu Ala Pro Thr Ala Glu Ala Ala Thr Glu Ala Pro Ala Ala
    50                  55                  60

Glu Ala Pro Ala Ala Glu Ala Ala Thr Glu Ala Pro Ala Ala Glu
65                  70                  75                  80

Ala Pro Ala Ala Glu Ala Pro Ala Ala Glu Ala Ala Lys
                85                  90

<210> SEQ ID NO 3
<211> LENGTH: 98
<212> TYPE: PRT
<213> ORGANISM: Neisseria meningitidis

<400> SEQUENCE: 3

Met Lys Lys Ser Leu Phe Ala Ala Ala Leu Leu Ser Leu Val Leu Ala
1               5                   10                  15

Ala Cys Gly Gly Glu Lys Ala Ala Glu Ala Pro Ala Ala Glu Ala Pro
                20                  25                  30

Ala Ala Glu Ala Pro Ala Thr Glu Ala Pro Ala Ala Glu Ala Pro Ala
            35                  40                  45

Ala Glu Ala Pro Ala Ala Glu Ala Pro Ala Thr Glu Ala Pro Ala Ala
    50                  55                  60

Glu Ala Pro Ala Ala Glu Ala Ala Thr Glu Ala Pro Ala Ala Glu
65                  70                  75                  80

Ala Ala Ala Thr Glu Ala Pro Ala Ala Glu Ala Pro Ala Ala Glu Ala
                85                  90                  95

Ala Lys

<210> SEQ ID NO 4
<211> LENGTH: 88
<212> TYPE: PRT
<213> ORGANISM: Neisseria gonorrhoeae

<400> SEQUENCE: 4

Met Lys Lys Ser Leu Phe Ala Ala Ala Leu Leu Ser Leu Ala Leu Ala
1               5                   10                  15

Ala Cys Gly Gly Glu Lys Ala Ala Glu Ala Pro Ala Ala Glu Ala Ser
                20                  25                  30
```

-continued

```
Ser Thr Glu Ala Pro Ala Ala Glu Ala Pro Ala Ala Glu Ala Pro Ala
         35                  40                  45

Ala Glu Ala Ala Ala Glu Ala Pro Ala Ala Glu Ala Pro Ala Ala
 50                  55                  60

Glu Ala Pro Ala Ala Glu Ala Ala Thr Glu Ala Pro Ala Ala Glu
 65                  70                  75                  80

Ala Pro Ala Ala Glu Ala Ala Lys
                 85

<210> SEQ ID NO 5
<211> LENGTH: 183
<212> TYPE: PRT
<213> ORGANISM: Neisseria meningitidis

<400> SEQUENCE: 5

Met Lys Ala Tyr Leu Ala Leu Ile Ser Ala Ala Val Ile Gly Leu Ala
 1               5                  10                  15

Ala Cys Ser Gln Glu Pro Ala Ala Pro Ala Ala Glu Ala Thr Pro Ala
                 20                  25                  30

Ala Glu Ala Pro Ala Ser Glu Ala Pro Ala Glu Ala Ala Pro Ala
         35                  40                  45

Asp Ala Ala Glu Ala Pro Ala Ala Gly Asn Cys Ala Ala Thr Val Glu
 50                  55                  60

Ser Asn Asp Asn Met Gln Phe Asn Thr Lys Asp Ile Gln Val Ser Lys
 65                  70                  75                  80

Ala Cys Lys Glu Phe Thr Ile Thr Leu Lys His Thr Gly Thr Gln Pro
                 85                  90                  95

Lys Ala Ser Met Gly His Asn Leu Val Ile Ala Lys Ala Glu Asp Met
                100                 105                 110

Asp Gly Val Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ala Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 6
<211> LENGTH: 201
<212> TYPE: PRT
<213> ORGANISM: Neisseria meningitidis

<400> SEQUENCE: 6

Met His Phe Asp Phe Cys Lys Thr Glu Tyr Tyr Phe Ile Asp Trp Arg
 1               5                  10                  15

Phe Thr Met Lys Ala Tyr Leu Ala Leu Ile Ser Ala Ala Val Ile Gly
                 20                  25                  30

Leu Ala Ala Cys Ser Gln Glu Pro Ala Ala Pro Ala Ala Glu Ala Thr
         35                  40                  45

Pro Ala Ala Glu Ala Pro Ala Ser Glu Ala Pro Ala Ala Glu Ala Ala
 50                  55                  60

Pro Ala Asp Ala Ala Glu Ala Pro Ala Ala Gly Asn Cys Ala Ala Thr
 65                  70                  75                  80
```

```
Val Glu Ser Asn Asp Asn Met Gln Phe Asn Thr Lys Asp Ile Gln Val
                85                  90                  95

Ser Lys Ala Cys Lys Glu Phe Thr Ile Thr Leu Lys His Thr Gly Thr
            100                 105                 110

Gln Pro Lys Ala Ser Met Gly His Asn Leu Val Ile Ala Lys Ala Glu
            115                 120                 125

Asp Met Asp Gly Val Phe Lys Asp Gly Val Gly Ala Ala Asp Thr Asp
        130                 135                 140

Tyr Val Lys Pro Asp Asp Ala Arg Val Val Ala His Thr Lys Leu Ile
145                 150                 155                 160

Gly Gly Gly Glu Glu Ser Ser Leu Thr Leu Asp Pro Ala Lys Leu Ala
                165                 170                 175

Asp Gly Asp Tyr Lys Phe Ala Cys Thr Phe Pro Gly His Gly Ala Leu
            180                 185                 190

Met Asn Gly Lys Val Thr Leu Val Asp
            195                 200
```

```
<210> SEQ ID NO 7
<211> LENGTH: 183
<212> TYPE: PRT
<213> ORGANISM: Neisseria meningitidis

<400> SEQUENCE: 7

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Glu Ala Thr Pro Ala
                20                  25                  30

Ala Glu Ala Pro Ala Ser Glu Ala Pro Ala Ala Glu Ala Ala Pro Ala
                35                  40                  45

Asp Ala Ala Glu Ala Pro Ala Ala Gly Asn Cys Ala Ala Thr Val Glu
            50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Thr Ser Met Gly His Asn Ile Val Ile Gly Lys Thr Glu Asp Met
            100                 105                 110

Asp Gly Ile Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180
```

```
<210> SEQ ID NO 8
<211> LENGTH: 183
<212> TYPE: PRT
<213> ORGANISM: Neisseria gonorrhoeae

<400> SEQUENCE: 8

Met Lys Ala Tyr Leu Ala Leu Ile Ser Ala Ala Val Ile Gly Leu Ala
1               5                   10                  15
```

```
Ala Cys Ser Gln Glu Pro Ala Ala Pro Ala Ala Glu Ala Thr Pro Ala
            20                  25                  30

Gly Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180
```

<210> SEQ ID NO 9
<211> LENGTH: 183
<212> TYPE: PRT
<213> ORGANISM: Neisseria gonorrhoeae

<400> SEQUENCE: 9

```
Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Gly Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180
```

<210> SEQ ID NO 10

```
<211> LENGTH: 5
<212> TYPE: PRT
<213> ORGANISM: Artificial sequence
<220> FEATURE:
<223> OTHER INFORMATION: synthetic

<400> SEQUENCE: 10

Ala Ala Glu Ala Pro
1               5

<210> SEQ ID NO 11
<211> LENGTH: 31
<212> TYPE: PRT
<213> ORGANISM: Artificial sequence
<220> FEATURE:
<223> OTHER INFORMATION: synthetic

<400> SEQUENCE: 11

Cys Ala Glu Ala Ala Ala Thr Glu Ala Pro Ala Ala Glu Ala Ala Ala
1               5                   10                  15

Thr Glu Ala Pro Ala Ala Glu Ala Pro Ala Ala Glu Ala Ala Lys
            20                  25                  30

<210> SEQ ID NO 12
<211> LENGTH: 31
<212> TYPE: PRT
<213> ORGANISM: Artificial sequence
<220> FEATURE:
<223> OTHER INFORMATION: synthetic

<400> SEQUENCE: 12

Cys Cys Gly Gly Glu Lys Ala Ala Glu Ala Pro Ala Ala Glu Ala Pro
1               5                   10                  15

Ala Ala Glu Ala Pro Ala Thr Glu Ala Pro Ala Ala Glu Ala Pro
            20                  25                  30

<210> SEQ ID NO 13
<211> LENGTH: 29
<212> TYPE: PRT
<213> ORGANISM: Artificial sequence
<220> FEATURE:
<223> OTHER INFORMATION: synthetic

<400> SEQUENCE: 13

Cys Gly Gly Glu Lys Ala Ala Glu Ala Pro Ala Ala Glu Ala Pro Ala
1               5                   10                  15

Ala Glu Ala Pro Ala Thr Glu Ala Pro Ala Ala Glu Ala
            20                  25
```

UNITED STATES PATENT AND TRADEMARK OFFICE
CERTIFICATE OF CORRECTION

PATENT NO.         : 9,475,864 B2                                                 Page 1 of 1
APPLICATION NO.    : 13/062181
DATED              : October 25, 2016
INVENTOR(S)        : Sanjay Ram et al.

It is certified that error appears in the above-identified patent and that said Letters Patent is hereby corrected as shown below:

In the Specification

Column 1, Lines 14 - 17 of the Patent should read as follows under Statement of Government Support:

This invention was made with government support under Grant numbers AI032725 and AI054544 awarded by the National Institutes of Health. The Government has certain rights in the invention.

Signed and Sealed this
Ninth Day of May, 2017

Michelle K. Lee
*Director of the United States Patent and Trademark Office*